United States Patent
Murtaza et al.

(10) Patent No.: US 10,683,538 B2
(45) Date of Patent: Jun. 16, 2020

(54) QUALITY ASSESSMENT OF CIRCULATING CELL-FREE DNA USING MULTIPLEXED DROPLET DIGITAL PCR

(71) Applicant: THE TRANSLATIONAL GENOMICS RESEARCH INSTITUTE, Phoenix, AZ (US)

(72) Inventors: Muhammed Murtaza, Phoenix, AZ (US); Tania Contente-Cuomo, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 277 days.

(21) Appl. No.: 15/565,869

(22) PCT Filed: Apr. 18, 2016

(86) PCT No.: PCT/US2016/028159
§ 371 (c)(1),
(2) Date: Oct. 11, 2017

(87) PCT Pub. No.: WO2016/168844
PCT Pub. Date: Oct. 20, 2016

(65) Prior Publication Data
US 2018/0105864 A1    Apr. 19, 2018

Related U.S. Application Data

(60) Provisional application No. 62/149,386, filed on Apr. 17, 2015.

(51) Int. Cl.
| | | |
|---|---|---|
| C12P 19/34 | (2006.01) | |
| C12Q 1/686 | (2018.01) | |
| C12Q 1/6806 | (2018.01) | |
| C12Q 1/6876 | (2018.01) | |
| C40B 40/06 | (2006.01) | |

(52) U.S. Cl.
CPC ......... *C12Q 1/686* (2013.01); *C12Q 1/6806* (2013.01); *C12Q 1/6876* (2013.01); *C40B 40/06* (2013.01); *B01J 2219/00587* (2013.01); *B01J 2219/00722* (2013.01); *C12Q 2525/204* (2013.01); *C12Q 2531/113* (2013.01); *C12Q 2545/101* (2013.01); *C12Q 2563/107* (2013.01); *C12Q 2563/159* (2013.01); *C12Q 2565/102* (2013.01); *C12Q 2565/629* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2011/0230358 A1 | 9/2011 | Rava | |
| 2011/0312504 A1* | 12/2011 | Driebe | C12Q 1/689 506/2 |
| 2012/0270739 A1 | 10/2012 | Rava et al. | |
| 2013/0224740 A1* | 8/2013 | Thierry | C12Q 1/6886 435/6.11 |
| 2014/0094373 A1 | 4/2014 | Zimmermann et al. | |
| 2015/0005176 A1 | 1/2015 | Kim et al. | |
| 2016/0186239 A1* | 6/2016 | Sinha | C12Q 1/686 506/9 |
| 2017/0152557 A1* | 6/2017 | Hamamah | C12Q 1/6883 |
| 2017/0327869 A1* | 11/2017 | Schutz | C12Q 1/686 |

FOREIGN PATENT DOCUMENTS

WO    2013/131021 A1    9/2013

OTHER PUBLICATIONS

Pinzani et al., "Circulating cell-free DNA in plasma of melanoma patients: Qualitative and quantitative considerations", Clinica Chimica Acta 412:2141-2145 (2011).

Yörüker et al., "Assessment of Circulating Serum DNA Integrity in Colorectal Cancer Patients", Anticancer Research, 35:2435-2440 (2015).

Bianchi, et al. DNA sequencing versus standard prenatal aneuploidy screening. The New England journal of medicine 2014;370:799-808.

Leary, et al. Detection of chromosomal alterations in the circulation of cancer patients with whole-genome sequencing. Science translational medicine 2012;4:162ra54.

Chan, et al. Cancer genome scanning in plasma: Detection of tumor-associated copy number aberrations, single-nucleotide variants, and tumoral heterogeneity by massively parallel sequencing. Clinical chemistry 2013;59:211-24.

Murtaza, et al. Non-invasive analysis of acquired resistance to cancer therapy by sequencing of plasma DNA. Nature 2013;497:108-12.

Chiu, et al. Non-invasive prenatal assessment of trisomy 21 by multiplexed maternal plasma DNA sequencing: Large scale validity study. Bmj 2011;342:c7401.

Lo, et al. Maternal plasma DNA sequencing reveals the genome-wide genetic and mutational profile of the fetus. Sci Transl Med 2010;2:61ra91.

(Continued)

*Primary Examiner* — Kenneth R Horlick
(74) *Attorney, Agent, or Firm* — Rodney J. Fuller; Booth Udall Fuller, PLC

(57) ABSTRACT

The present invention provides a method of determining integrity and/or quantity of cell free DNA (cfDNA) in a biological sample comprising amplifying target sequences with at least a first primer/probe set and at least a second primer probe/set, amplifying the target sequences of differing lengths, and monitoring for detection of the labels of the oligonucleotide probes, and determining the integrity and/or quantity of the cfDNA based on the level of detection of the label of the oligonucleotide probe from the first primer/probe set compared to the level detection of the label of the oligonucleotide probe from the second primer/probe set. The present invention also provides methods for generating a library with the cfDNA for sequencing and analysis.

19 Claims, 19 Drawing Sheets

Specification includes a Sequence Listing.

(56) References Cited

OTHER PUBLICATIONS

De Vlaminck, et al. Circulating cell-free DNA enables noninvasive diagnosis of heart transplant rejection. Sci Transl Med 2014;6:241ra77.

Forshew, et al. Noninvasive identification and monitoring of cancer mutations by targeted deep sequencing of plasma DNA. Science translational medicine 2012;4:136ra68.

Dawson, et al. Analysis of circulating tumor DNA to monitor metastatic breast cancer. The New England journal of medicine 2013;368:1199-209.

Bettegowda, et al. Detection of circulating tumor DNA in early- and late-stage human malignancies. Science translational medicine 2014;6:224ra24.

Devonshire, et al. Towards standardisation of cell-free DNA measurement in plasma: controls for extraction efficiency, fragment size bias and quantification. Analytical and Bioanalytical Chemistry. 2014;406(26):6499-6512.

\* cited by examiner

FIG. 1

Large Amplicon

| SEQ ID NO: | Type | Sequence | Start | Length | Tm | GC Percent | Amplicon bp |
|---|---|---|---|---|---|---|---|
| 1 | Forward Primer | TCTATGCTCCCTCTGTGTTAGA | 1997 | 22 | 62.108 | 45.455 | 439 |
| 2 | Probe | AGCAAGGTGCCCTGAGAAGACAAT | 2244 | 24 | 68.02 | 50 | |
| 3 | Reverse Primer | TCCAGGAATTCACCCGAAAC | 2435 | 20 | 62.146 | 50 | |

| SEQ ID NO: | Type | Sequence | Start | Length | Tm | GC Percent | Amplicon bp |
|---|---|---|---|---|---|---|---|
| 4 | Forward Primer | CAGACAAGATGAGGAGGTACAAA | 2570 | 23 | 61.899 | 43.478 | 444 |
| 5 | Probe | ATTGAGCCTGTGCCTGGCTAGAAA | 2815 | 24 | 68.045 | 50 | |
| 6 | Reverse Primer | AGCTGTGAGTAGAGGAGTCTT | 3013 | 21 | 61.988 | 47.619 | |

| SEQ ID NO: | Type | Sequence | Start | Length | Tm | GC Percent | Amplicon bp |
|---|---|---|---|---|---|---|---|
| 7 | Forward Primer | AAAGAGGTCTTGCCAGGTATTC | 2152 | 22 | 62.235 | 45.455 | 522 |
| 8 | Probe | ATAGGGCTTCAGGCCAAACATGGT | 2426 | 24 | 68.239 | 50 | |
| 9 | Reverse Primer | AGCTCACTGCAGCCTTAATC | 2673 | 20 | 62.215 | 50 | |

FIG. 1 (continued)

| SEQ ID NO: | Type | Sequence | Start | Length | Tm | GC Percent | Amplicon bp |
|---|---|---|---|---|---|---|---|
| 10 | Forward Primer | GTCTCCAGGATAGCTGCTTATG | 557 | 22 | 62 | 50 | 480 |
| 11 | Probe | TTTGGGACTGGCCTTTGAAGCTCT | 828 | 24 | 68 | 50 | |
| 12 | Reverse Primer | TGCATGTGAGCACCAAGT | 1019 | 18 | 62 | 50 | |

Small Amplicon

| SEQ ID NO: | Type | Sequence | Start | Length | Tm | GC Percent | Amplicon bp |
|---|---|---|---|---|---|---|---|
| 13 | Forward Primer | CTTGTACCTGGGTGTTCGGTTAT | 282 | 22 | 62.118 | 45.455 | 70 |
| 14 | Probe | AGCCTCTCCTCTGCAACCTGATA | 306 | 25 | 68.04 | 52 | |
| 15 | Reverse Primer | GTAGGCTGGGTAGCCAAATC | 351 | 20 | 62.132 | 55 | |

| SEQ ID NO: | Type | Sequence | Start | Length | Tm | GC Percent | Amplicon bp |
|---|---|---|---|---|---|---|---|
| 16 | Forward Primer | CCAGCCCAAGATGGATGAAT | 515 | 20 | 62.171 | 50 | 67 |
| 17 | Probe | TGCAGTTGTTCCGAGGTGACACA | 535 | 23 | 68.081 | 52.174 | |
| 18 | Reverse Primer | CTCTCTTTCCTTTCAGCAACAC | 580 | 23 | 61.902 | 43.478 | |

FIG. 1 (continued)

| SEQ ID NO: | Type | Sequence | Start | Length | Tm | GC Percent | Amplicon bp |
|---|---|---|---|---|---|---|---|
| 19 | Forward Primer | GCGGTGGAAGTCATTCTGATA | 1153 | 21 | 61.918 | 47.619 | 71 |
| 20 | Probe | TGGAGTTGGCATTGGAAGCTTATTCT | 1174 | 26 | 66.655 | 42.308 | |
| 21 | Reverse Primer | TCTCTCTCTCCAGTGAACAA | 1223 | 22 | 62.185 | 45.455 | |

| SEQ ID NO: | Type | Sequence | Start | Length | Tm | GC Percent | Amplicon bp |
|---|---|---|---|---|---|---|---|
| 22 | Forward Primer | GAGGGCCACAGATTGGTATT | 1729 | 20 | 62 | 50 | 71 |
| 23 | Probe | AATGAGATACGAGGGTTGTTGCTGGG | 1749 | 26 | 68 | 50 | |
| 24 | Reverse Primer | GATCACTTAGCTCAGGAAACAAAC | 1776 | 24 | 62 | 42 | |

| SEQ ID NO: | Type | Sequence | Start | Length | Tm | GC Percent | Amplicon bp |
|---|---|---|---|---|---|---|---|
| 25 | Forward Primer | ACTGAAAGGTCAGATTCAGGAG | 399 | 22 | 62 | 46 | 75 |
| 26 | Probe | ATCGCCTTGATCAACAGCCTCCA | 424 | 23 | 68 | 52 | |
| 27 | Reverse Primer | TACCGGTTTGTGTCCAAGAG | 454 | 20 | 62 | 50 | |

FIG. 4

Example input:
- 50 haploid copies cfDNA average fragment size ~180 bp
- 20 haploid copies background DNA from peripheral blood cells (intact)

Expected results:

🔵 FAM  50 + 20 = 70 × 5 short amplicons = 350 FAM+ droplets

🔵 TET  20 × 4 long amplicons = 80 TET+ droplets $$\frac{\text{FAM}}{5} \div \frac{\text{TET}}{4} \sim \text{Amplifiable copies of LMW cfDNA}$$

100
QUALITY ASSESSMENT OF CIRCULATING CELL-FREE DNA USING MULTIPLEXED DROPLET DIGITAL PCR

CROSS REFERENCE TO RELATED APPLICATIONS

This application is the U.S. National Stake of International Application No. PCT/US2016/028159 filed Apr. 18, 2016, which claims priority to and the benefit of U.S. Provisional Application No. 62/149,386 filed Apr. 17, 2015, the contents of each of which are hereby incorporated by reference in their entireties.

REFERENCE TO SEQUENCE LISTING SUBMITTED ELECTRONICALLY

The official copy of the sequence listing is submitted electronically via EFS-Web as an ASCII-formatted sequence listing with a file named "91482_179_Seq_Listing_ST25.txt" created on Apr. 14, 2016, and having a size of 6 kilobytes, and is filed concurrently with the specification. The sequence listing contained in this ASCII-formatted document is part of the specification and is herein incorporated by reference in its entirety.

TECHNICAL FIELD

The present invention is related to methods of assessing the integrity and quantity of cell-free DNA in biological samples.

BACKGROUND

Analysis of circulating cell-free DNA (cfDNA) in plasma has several established and upcoming diagnostic applications in prenatal, cancer and transplant medicine (1-7). Whole-genome sequencing of cfDNA is clinically available for noninvasive prenatal screening of fetal aneuploidies (1, 5). Next-generation sequencing of cfDNA in cancer patients can enable noninvasive identification of cancer mutations, monitoring of cancer burden and tumor evolution (4, 8-10). However, little is understood about the effect of pre-analytical factors on DNA quality and on performance of molecular assays.

Informative fraction of cfDNA is generally fragmented with a modal size of 160-180 bp. Pre-analytical factors such as delayed fractionation of plasma or incomplete removal of peripheral blood cells before freezing can cause an increase in higher molecular weight (HMW) DNA fraction from cell lysis. For PCR-based sequencing approaches, this can artificially lower the fraction of the target alleles such as a tumor-specific mutations in circulating tumor DNA making its detection more challenging and causing errors in its quantification. Since cfDNA is fragmented in vivo, ligation-mediated preparation of sequencing libraries from cfDNA does not involve shearing, and therefore HMW DNA is not incorporated into sequencing libraries. If the upfront measurement of total cfDNA is erroneously high due to a large fraction of HMW DNA downstream sequencing can be compromised.

Quantification of cfDNA can be performed using fluorometric or spectrophotometric methods such as QUBIT® (Life Technologies) or NANODROP™ (Thermo Scientific). These methods do not measure DNA size and cannot account for a HMW fraction in plasma DNA. Electrophoretic methods can perform size-based quantification but require input amounts for reliable results that are not feasible for cfDNA analysis. In addition, none of these methods provide an assessment of amplifiable DNA copies available for downstream molecular analysis. Multiplexed quantitative PCR can provide an assessment of size and amplifiable DNA but requires comparison with a standard curve. It relies on 1-2 genomic loci to infer total cfDNA content assuming that the targeted loci are single-copy genes. This assumption can affect measurement of cfDNA from cancer patients with somatic copy number changes reflected in plasma. In addition, it was recently shown that relative readouts from multiple single-locus assays can vary systematically potentially due to assay performance and variable stability across genomic DNA (11)

An efficient method for accurate quantification of cfDNA and assessment of cfDNA integrity is needed. As the amounts of cfDNA available in a sample are generally very limited, such a method requires a relatively wide dynamic range and the capability to detect and assess minute amounts of cfDNA.

SUMMARY

The present invention is directed to a method of determining integrity and/or quantity of cell free DNA (cfDNA) in a biological sample, the method comprising the steps of: a) obtaining a biological sample comprising cfDNA; b) contacting the biological sample with at least a first primer/probe set and at least a second primer probe/set, each of which comprises at least one oligonucleotide probe that is detectably labeled and at least two oligonucleotide primers and the labels are different for each primer/probe set, under conditions such that the first primer/probe set anneals to a first target sequence of less than 300 bp in length and the second primer/probe set anneals to a second target sequence of 300 bp or greater in length; c) amplifying, if present, the first target sequence and the second target sequence; and d) monitoring for detection of the label of the oligonucleotide probe from the first primer/probe set as an indication of hybridization to the first target sequence and detection of the label of the oligonucleotide probe from the second primer/probe set as an indication of hybridization to the second target sequence; and e) determining the integrity and/or quantity of the cfDNA based on the level of detection of the label of the oligonucleotide probe from the first primer/probe set compared to the level detection of the label of the oligonucleotide probe from the second primer/probe set, wherein a greater level of detection of the label of the oligonucleotide probe from the first primer/probe set compared to the level of detection of the label of the oligonucleotide probe from the second primer/probe set indicates increased integrity and/or quantity of cfDNA in the biological sample.

In some aspect, the oligonucleotide primers have a nucleotide sequence length of about 10 to about 150. In other aspects, the oligonucleotide probes have a nucleotide sequence length of about 10 to about 50.

In certain embodiments, the first target sequence and the second target sequence are from at least one housekeeping gene. In one embodiment, the at least one housekeeping gene is selected from the group consisting of ACTB (Beta-actin), GAPDH (Glyceraldehyde 3-phosphate dehydrogenase), RPLP0 (60 S acidic ribosomal protein P0), GUSB (beta-glucuronidase), and TFRC (transferring receptor 1).

In some aspects, the first primer/probe set comprises at least one oligonucleotide probe and at least two oligonucleotide primers each comprising an oligonucleotide sequence selected from the group consisting of SEQ ID NOs: 13-27.

In other aspects, the second primer/probe set comprises at least one oligonucleotide probe and at least two oligonucleotide primers each comprising an oligonucleotide sequence selected from the group consisting of SEQ ID NOs: 1-12.

In one embodiment, the first primer/probe set comprises at least two, at least three, at least four, or at least five oligonucleotide probes that are detectably labeled and at least four, at least six, at least eight, or at least 10 oligonucleotide primers, each of which anneals to a target sequence of less than 300 bp.

In another embodiment, the second primer/probe set comprises at least two, at least three, at least four, or at least five oligonucleotide probes that are detectably labeled and at least four, at least six, at least eight, or at least 10 oligonucleotide primers, each of which anneals to a target sequence of 300 bp or greater in length.

In some aspects, detection of the labels of the oligonucleotide probes from the first primer probe/set and/or second primer/probe set are averaged across each primer/probe set to determine the detection of the labels.

In yet other aspects, the amplifying of the target sequences occurs with a digital PCR technique selected from droplet digital PCR (ddPCR), BEAMing (beads, emulsion, amplification, and magnetic), and microfluidic chips. In a particular embodiment, the digital PCR technique is multiplexed ddPCR.

In one aspect, amplifiable copies (ACs) of cfDNA in the biological sample are estimated by: (i) dividing the number of positive droplets indicating hybridization to the first target sequence by the number of oligonucleotide probes in the first primer/probe set; (ii) dividing the number of positive droplets indicating hybridization to the second target sequence by the number of oligonucleotide probes in the second primer/probe set; and (iii) subtracting (ii) from (i) to estimate ACs of cfDNA in the biological sample.

In certain aspects, the oligonucleotide probes are detectably labeled with a fluorescent label selected from the group consisting of FAM™ (5- or 6-carboxyfluorescein), Fluorescein, TET™ (5-tetrachloro-fluorescein), MARINA BLUE® (6,8-difluoro-7-hydroxy-4-methylcoumarin), ALEXA FLUOR® 350 (7-amino-4-methyl-6-sulfocoumarin-3-acetic acid), YAKIMA YELLOW® (2',5,5',6-tetrachloro-7'-{12-[di(propan-2-yl)amino]-15-hydroxy-3-oxo-11,13-dioxa-4-aza-12-phosphapentadecyl}-4'-methyl-3-oxo-3H-spiro[2-benzofuran-1,9'-xanthene]-3',6'-diyl bis(2,2-dimethylpropanoate), and TEXAS RED® (sulforhodamine sulfonyl chloride).

In one embodiment, the fluorescent labels are FAM™ (5- or 6-carboxyfluorescein) and TET™ (5-tetrachloro-fluorescein).

In yet another embodiment, the first primer/probe set detects at least one, at least two, at least three, at least four, or at least five target sequences of about 50 bp to about 100 bp in length. In one aspect, the second primer/probe set detects at least one, at least two, at least three, at least four, or at least five target sequences of about 300 bp to about 1000 bp in length.

In some aspects, the method further comprises generating a library with the cfDNA for sequencing and analysis. In one embodiment, the library is an exome library.

In other aspects, the biological sample is divided into aliquots and each aliquot undergoes a different upstream process to evaluate how upstream processing affects the integrity and/or quantity of cfDNA in the biological sample.

In some embodiments, biological samples from different study cohorts are evaluated to determine the integrity and/or quality of the cfDNA in the biological samples from each cohort.

In yet other embodiments, the biological sample is a biofluid selected from the group consisting of blood, plasma, serum, saliva, urine, tears, and cerebral spinal fluid.

In one aspect, detection of the labels of the oligonucleotide probes occurs with a flow cytometer or a droplet reader.

In yet another aspect, the method further comprises performing an amplification with the first primer/probe set and/or the second primer/probe set without the biological sample as a negative control.

BRIEF DESCRIPTION OF THE DRAWINGS

FIG. 1 shows primer and probe sequences that can be used to quantify and assess the integrity of cfDNA. The lengths of the primers and probes, their melting temperatures ("Tm"), and GC content ("GC percent") are also indicated along with the length of the resulting amplicons ("Amplicon bp").

FIG. 4 depicts a sample calculation of the number of amplifiable copies of low molecular weight (LMW) cfDNA in a hypothetical biological sample containing 50 haploid copies of cfDNA with an average fragment size of about 180 bp and 20 haploid copies of DNA from intact peripheral blood cells. The calculation is based on the ddPCR assay design shown in FIG. 3.

DETAILED DESCRIPTION

Figure 2:
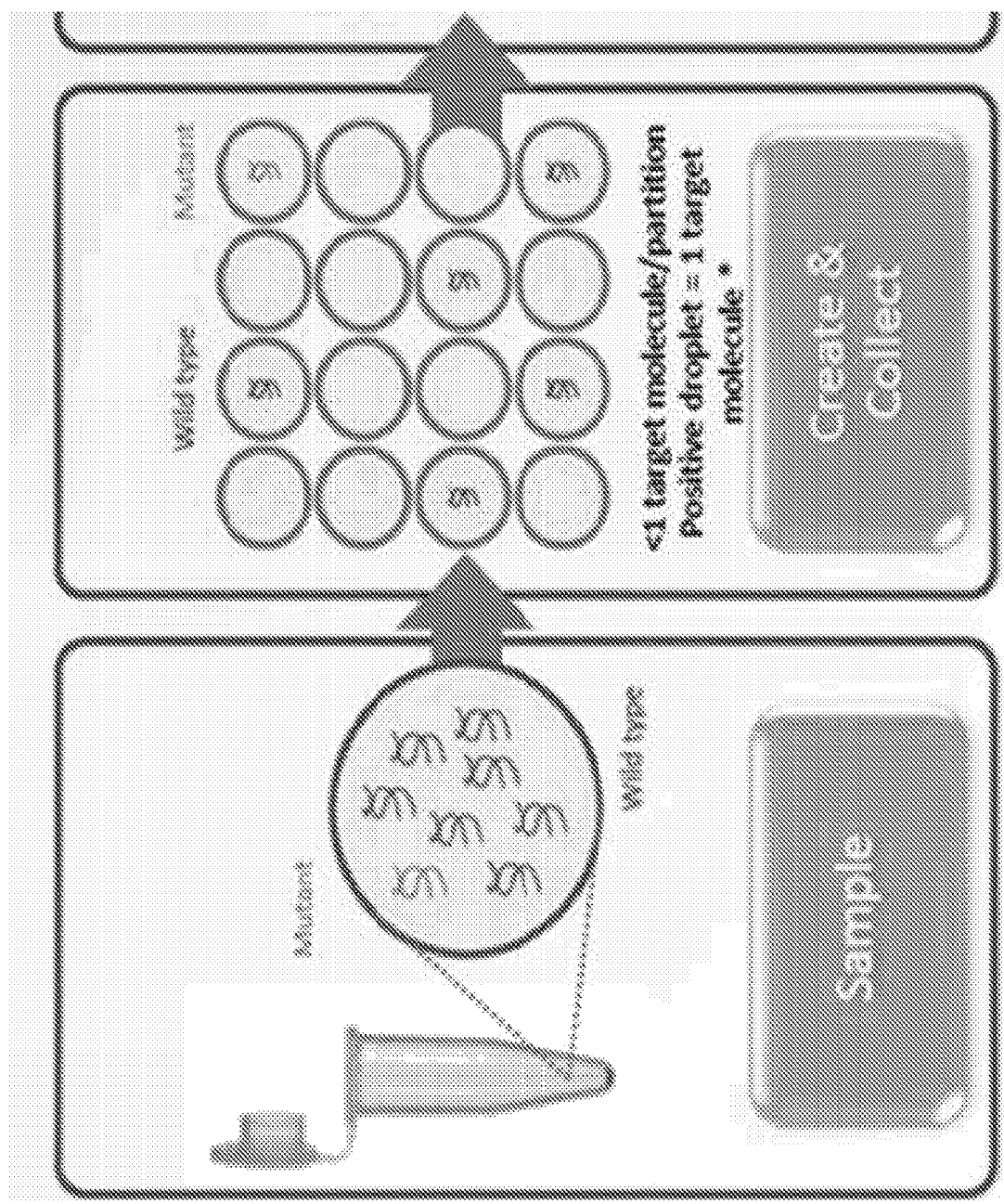
FIG. 2 depicts the steps involved in one form of droplet digital PCR (ddPCR). In this figure, the sample contains a mixture of genomic DNA with a mutant gene and genomic DNA with the corresponding wild type gene. The ddPCR is designed to amplify and detect relative amounts of each form of the gene with specific fluorescent probes.
Figure 2:
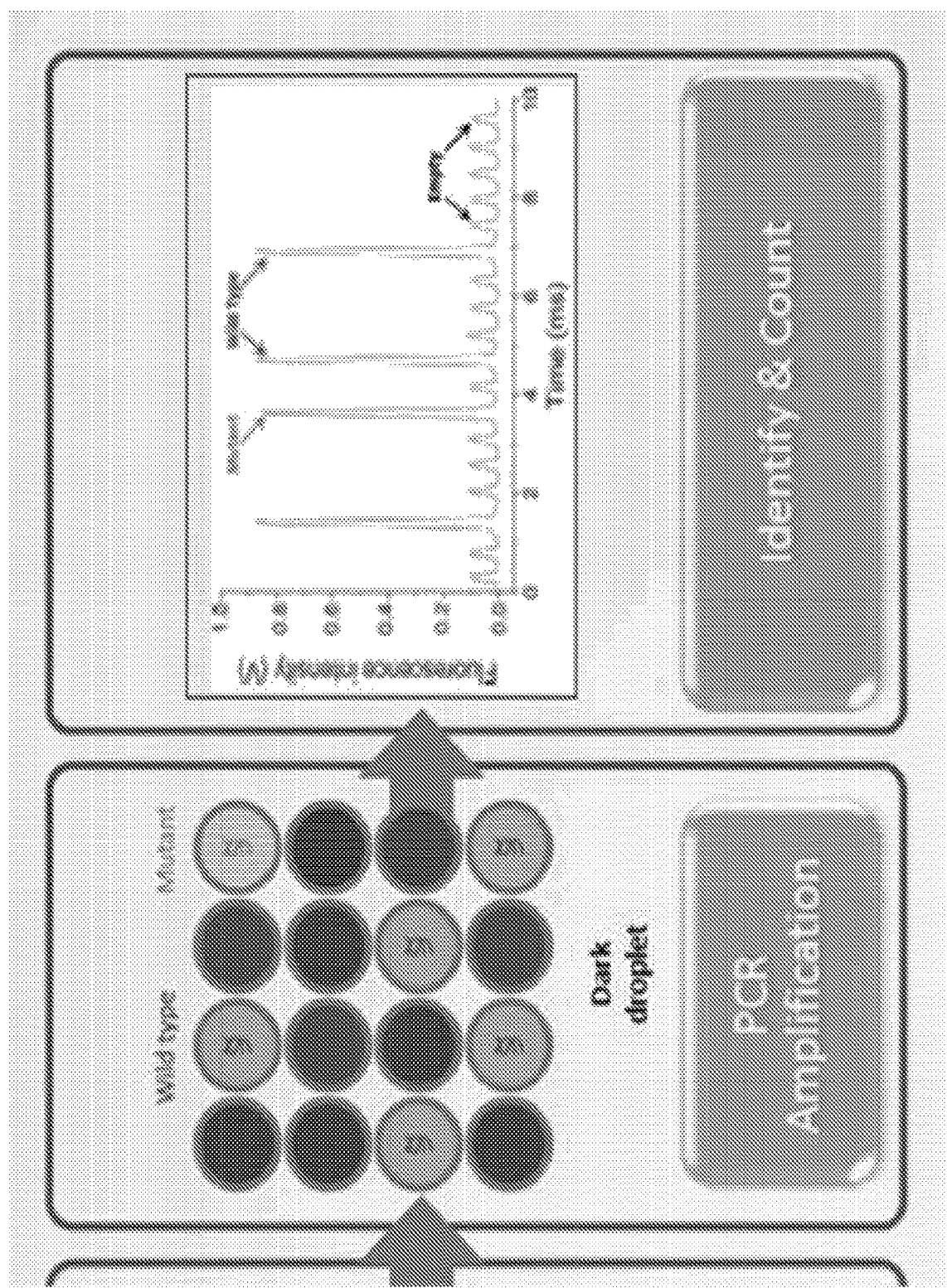

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, "primer/probe set" refers to a grouping of a pair of oligonucleotide primers and an oligonucleotide probe that hybridize to a specific nucleotide sequence. Said oligonucleotide set consists of: (a) a forward discriminatory primer that hybridizes to a first location of a nucleic acid sequence; (b) a reverse discriminatory primer that hybridizes to a second location of the nucleic acid sequence downstream of the first location and (c) a fluorescent probe labeled with a fluorophore and a quencher, which hybridizes to a location of the nucleic acid sequence between the primers. In other words, a primer/probe set consists of a set of specific PCR primers capable of initiating synthesis of an amplicon specific to a nucleic acid sequence, and a fluorescent probe which hybridizes to the amplicon.

An "amplicon" refers to a nucleic acid fragment formed as a product of natural or artificial amplification events or techniques. For example, an amplicon can be produced by PCR, ligase chain reaction, or gene duplication.

The terms "short amplicon" and "small amplicon" used herein are synonymous and refer to amplicons having a length less than 300 bp.

The terms "long amplicon" and "large amplicon" used herein are synonymous and refer to amplicons having a length greater than or equal to 300 bp.

A "probe" or "fluorogenic probe" comprises an oligonucleotide sequence labeled with both a "fluorescent reporter dye", or "fluorophore", and a "quencher dye", or "quencher." A "fluorescent reporter dye" or "fluorophore" refers to a molecule that emits light of a certain wavelength after having first absorbed light of a specific, but shorter, wavelength, wherein the emission wavelength is always higher than the absorption wavelength. A "quencher dye" "quencher" refers to a molecule that accepts energy from a fluorophore in the form of light at a particular wavelength and dissipates this energy either in the form of heat (e.g., proximal quenching) or light of a higher wavelength than emitted from the fluorophore (e.g., FRET quenching). Quenchers generally have a quenching capacity throughout their absorption spectrum, but they perform best close to their absorption maximum. For example, Deep Dark Quencher II absorbs over a large range of the visible spectrum and, consequently, efficiently quenches most of the commonly used fluorophores, especially those emitting at higher wavelengths (like the Cy® dyes). Similarly, the Black Hole Quencher family covers a large range of wavelengths (over the entire visible spectrum and into the near-IR). In contrast, Deep Dark Quencher I and Eclipse® Dark Quencher effectively quench the lower wavelength dyes, such as FAM, but do not quench very effectively those dyes that emit at high wavelengths.

The term "housekeeping genes" as used herein is meant to refer to genes that encode protein products that are not connected to, involved in or required for processes specific to a disease state (e.g., cancer) in cells, and thus, exhibit a fixed expression level in diseased and healthy cells. Examples of suitable housekeeping genes include, but are not limited to, genes encoding ACTB (Beta-actin), GAPDH (Glyceraldehyde 3-phosphate dehydrogenase), RPLP0 (60 S acidic ribosomal protein P0), GUSB (beta-glucuronidase), and TFRC (transferring receptor 1).

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some implementations, the subject may be a mammal, preferably a human.

As used herein, "digital PCR" refers to an assay that provides an end-point measurement that provides the ability to quantify nucleic acids without the use of standard curves, as is used in real-time PCR. In a typical digital PCR experiment, the sample is randomly distributed into discrete partitions, such that some contain no nucleic acid template and others contain one or more template copies. The partitions are amplified to the terminal plateau phase of PCR (or end-point) and then read to determine the fraction of positive partitions. If the partitions are of uniform volume, the number of target DNA molecules present may be calculated from the fraction of positive end-point reactions using Poisson statistics, according to the following equation:

$$\lambda = -\ln(1-p) \quad (1)$$

wherein $\lambda$, is the average number of target DNA molecules per replicate reaction and p is the fraction of positive end-point reactions. From $\lambda$, together with the volume of each replicate PCR and the total number of replicates analyzed, an estimate of the absolute target DNA concentration is calculated. Digital PCR includes a variety of formats, including droplet digital PCR, BEAMing (beads, emulsion, amplification, and magnetic), and microfluidic chips.

"Droplet digital PCR" (ddPCR) refers to a digital PCR assay that measures absolute quantities by counting nucleic acid molecules encapsulated in discrete, volumetrically defined, water-in-oil droplet partitions that support PCR amplification (Hinson et al., 2011, Anal. Chem. 83:8604-8610; Pinheiro et al., 2012, Anal. Chem. 84:1003-1011). A single ddPCR reaction may be comprised of at least 20,000 partitioned droplets per well.

A "droplet" or "water-in-oil droplet" refers to an individual partition of the droplet digital PCR assay. A droplet supports PCR amplification of template molecule(s) using homogenous assay chemistries and workflows similar to those widely used for real-time PCR applications (Hinson et al., 2011, Anal. Chem. 83:8604-8610; Pinheiro et al., 2012, Anal. Chem. 84:1003-1011).

Droplet digital PCR may be performed using any platform that performs a digital PCR assay that measures absolute quantities by counting nucleic acid molecules encapsulated in discrete, volumetrically defined, water-in-oil droplet partitions that support PCR amplification. The strategy for droplet digital PCR may be summarized as follows: a sample is diluted and partitioned into thousands to millions of separate reaction chambers (water-in-oil droplets) so that each contains one or no copies of the nucleic acid molecule of interest. The number of "positive" droplets detected, which contain the target amplicon (i.e., nucleic acid molecule of interest), versus the number of "negative" droplets, which do not contain the target amplicon (i.e., nucleic acid molecule of interest), may be used to determine the number of copies of the nucleic acid molecule of interest that were in the original sample. Examples of droplet digital PCR systems include the QX100™ Droplet Digital PCR System by Bio-Rad, which partitions samples containing nucleic acid template into 20,000 nanoliter-sized droplets; and the RainDrop™ digital PCR system by RainDance, which partitions samples containing nucleic acid template into 1,000,000 to 10,000,000 picoliter-sized droplets.

In some aspects, the present invention provides a method to perform one-step quantification of DNA and assessment of DNA integrity (measurement of BMW and cfDNA fractions) using a 9-plex multiplexed approach using ddPCR. Instead of measuring individual loci, the assay relies on the average readout of all tested loci, measuring the concentration of cfDNA and HMW DNA with high precision and accuracy. cfDNA quantification using this approach predicts downstream performance of ligation-mediated exome sequencing.

In other aspects, the present invention provides an approach for accurate one-step assessment of DNA quantity and integrity from minute amounts of cell-free DNA using picoliter droplet digital PCR (ddPCR).

Ins some embodiments, a multiplexed ddPCR assay including primers and sequence-specific oligonucleotide probes to target 5 short amplicons (67-71 bp) and 4 long amplicons (439-522 bp) from independent quiescent regions of the human genome is provided. In one embodiment, all short and long amplicon probes are labeled with fluorescent dyes FAM and TET, respectively. Amplifiable DNA fragments using short and long amplicons are calculated as the average across each set, to increase precision and accuracy when evaluating small input amounts of DNA. The assay performance may be evaluated using control genomic DNA sheared by sonication to average fragment sizes of 150-1000 bp. 15 ligation-based exome sequencing libraries from control plasma DNA samples, guided by ddPCR DNA integrity assessment without further shearing were prepared to validate the assay.

In some aspects, relative quantities of amplifiable fragments using short and long PCR reflect integrity of sheared genomic DNA, approximately following expectations of the exponential distribution for DNA fragmentation. Accurate quantification and assessment of integrity is achievable using picogram amounts of cell-free DNA (as few as 200 pg). DNA integrity and quantity assessments are predictive of library diversity and obtainable depth-of-coverage in next-generation sequencing libraries made from cell-free DNA samples.

As novel diagnostic applications of circulating cell-free DNA are evaluated for clinical relevance, reliable assays for assessment of DNA quality are needed to objectively account for pre-analytical variation. The present invention provides an accurate and precise droplet digital PCR approach to practically implement quality assurance for clinical cell-free DNA studies.

In certain aspects, the present invention is directed to a method of determining integrity of nucleic acid sample, the method comprising the steps of: obtaining a sample comprising nucleic acids; amplifying from the sample a plurality of first markers to provide a plurality of first amplicons using at least one first oligonucleotide, wherein the first oligonucleotide comprises a first dye; amplifying from the sample a plurality of second markers to provide a plurality of second amplicons using at least one second oligonucleotide, wherein the second oligonucleotide comprises a second dye wherein, the first dye and the second dye are different dyes; and comparing a dye intensity level from the amplification of the plurality of first markers to a dye intensity level from the amplification of the plurality of second markers.

In certain aspects, the nucleic acids are DNA. In other aspects, the nucleic acids are cell free DNA. In one embodiment, the first dye is FAM. In another embodiment, the second dye is TET.

In certain aspects, the plurality of first amplicons are between about 1 and 180 base pairs in length. In other aspects, the plurality of first amplicons are between about 50 and about 70 based pairs in length. In yet other aspects, the plurality of second amplicons are between about 250 and 1,000 base pairs in length. In one embodiment, the plurality of second amplicons are between about 400 and 500 base pairs in length.

In some embodiments, the plurality of first markers consists of between 4 and 10 markers. In other embodiments, plurality of first markers consists of between 5 and 7 markers. In yet other embodiments, the plurality of second markers consists of between 4 and 10 markers. In one aspect, the plurality of second markers consists of between 4 and 7 markers.

In some aspects, the method further comprises sequencing at least a portion of the nucleic acids in the sample. In one aspect, an amount of the sample sequenced is at least partially determined based on the comparison of the dye intensity levels. In some embodiments, the sequencing comprises whole exome sequencing.

In other aspects, the method further comprises performing an amplification using at least one first oligonucleotide without the sample as a negative control. In one aspect, the method further comprises performing an amplification using at least one second oligonucleotide without the sample as a negative control.

In some embodiments, the amplification steps occur during one or more PCR reactions. In one aspect, the PCR is digital PCR. In another aspect, the digital PCR is droplet digital PCR.

The present invention is also related to a method of selecting a plurality of first markers and a plurality of second markers for determining integrity of a nucleic acid sample, the method comprising the steps of: obtaining expression information on a genomic scale for potential markers; selecting the plurality of first markers based on the expression information, wherein the plurality of first markers are selected based on conditions in which the first markers are expressed; and selecting the plurality of second markers based on the expression information, wherein the plurality of second markers are selected based on conditions in which the second markers are expressed, wherein the plurality of first markers and the plurality of second markers do not overlap.

In one embodiment, the expression information is obtained from at least one of one or more databases, RNA sequencing analysis, microarrays, and reverse transcriptase PCR experiments.

In yet other aspects, the present invention is directed to a method of determining integrity of nucleic acid sample, the method comprising the steps of: obtaining a sample comprising nucleic acids; amplifying from the sample a plurality of first markers to provide a plurality of first amplicons using at least one first oligonucleotide, wherein the plurality of first amplicons are between about 1 and 180 base pairs in length; amplifying from the sample a plurality of second markers to provide a plurality of second amplicons using at least one second oligonucleotide, wherein the plurality of second amplicons are between about 250 and 1,000 base pairs in length; and comparing a mass of the plurality of the first amplicons to a mass of the plurality of second amplicons.

In certain aspects, the label on the oligonucleotide probe is a fluorescent label and the label is selected from the group of FAM™ (5- or 6-carboxyfluorescein), Fluorescein, TET™ (5-tetrachloro-fluorescein), MARINA BLUE® (6,8-difluoro-7-hydroxy-4-methylcoumarin), ALEXA FLUOR® 350 (7-amino-4-methyl-6-sulfocoumarin-3-acetic acid), YAKIMA YELLOW® (2',5,5',6-tetrachloro-7'-{12-[di(propan-2-yl)amino]-15-hydroxy-3-oxo-11,13-dioxa-4-aza-12-phosphapentadecyl}-4'-methyl-3-oxo-3H-spiro[2-benzofuran-1,9'-xanthene]-3',6'-diyl bis(2,2-dimethylpropanoate), and TEXAS RED® (sulforhodamine sulfonyl chloride). Fluorescent labels (i.e., dyes) along with their channel for detection and the excitation and detection wavelengths are provided in Table 1.

TABLE 1

| Channel | Excitation source/Detection filter | Detected Dyes (Examples) |
| --- | --- | --- |
| Blue | 365 ± 20 nm/460 ± 15 nm | MARINA BLUE ®, (6,8-difluoro-7-hydroxy-4-methylcoumarin), ALEXA FLOUR ® 350 (7-amino-4-methyl-6-sulfocoumarin-3-acetic acid) |
| Green | 470 ± 10 nm/510 ± 5 nm | FAM ™, (5- or 6-carboxyfluorescein), Fluorescein |
| Yellow | 530 ± 5 nm/555 ± 5 nm | TET ™ (5-tetrachloro-fluorescein), YAKIMA YELLOW ® (2',5,5',6-tetrachloro-7'-{12-[di(propan-2-yl)amino]-15-hydroxy-3-oxo-11,13-dioxa-4-aza-12-phosphapentadecyl}-4'-methyl-3-oxo-3H-spiro[2-benzofuran-1,9'-xanthane]-3',6'-diyl bis(2,2-dimethylpropanoate) |
| Orange | 585 ± 5 nm/610 ± 5 nm | TEXAS RED ® (sulforhodamine sulfonyl chloride) |
| Red | 625 ± 10 nm/660 ± 10 nm | |
| Crimson | 680 ± 5 nm/712 long pass | |

There is now strong evidence that the level of fetal cfDNA (and/or total cfDNA) present in the circulatory system (e.g. in plasma) of a pregnant female is a marker of one or more forms of preeclampsia, such as early-onset preeclampsia, mild and/or severe preeclampsia. The present invention shows particular utility in the efficient, effective, sensitive and/or low-variability detection/quantification of fetal cfDNA present in plasma of pregnant females, and the present invention has particular utility therein. Accordingly, in particular embodiments of the present invention, the subject is a pregnant female and is susceptible to suffering or developing a pregnancy-associated medical condition; particularly where said pregnancy-associated medical condition is preeclampsia. As used herein, a subject "susceptible to" a medical condition may alternatively be described as "is suspected to" or to "be considered at risk of being susceptible to" suffering or developing a medical condition; and in certain embodiments, the present invention is used to screen and/or diagnose the individual for susceptibility to, risk of suffering or developing, or suffering from or developing, a medical condition.

In alternative embodiments, the individual is a pregnant female and is susceptible to (or considered at risk of being susceptible to) suffering or developing a pregnancy-associated medical condition selected from the group consisting of: preterm labor, intrauterine growth retardation and vanishing twin. The present invention may also be utilized in gender determination of twin pregnancies, by consideration of the relative values for fetal cfDNA compared to counts of Y-chromosome sequences determined from cfDNA (e.g., by using parallel sequencing approaches). In these regards, it should be noted that approaches that use massively-parallel sequencing of random cfDNA in maternal blood typically always count a very low frequency of "Y-chomomosone" sequences (such as between about 0.003% and 0.004% of all sequences, or between about 0.0015% and 0.01% or 0.002% and 0.005% of all sequences) in all female pregnancies due to homology of certain Y-chromosome short sequences to other chromosomes. A cut off "Y-chromosome" sequence counts of about 0.005%, or between about 0.003%, 0.004%, 0.006% or 0.007%, may therefore be employed for female samples.

As described elsewhere herein, there is also increasing evidence that the presence and amount of certain forms of cfDNA is indicative or prognostic of certain medical conditions that are not associated with pregnancy. Accordingly, in another particular embodiment of the present invention, said species of DNA originates from a cell type associated with such a medical condition, particularly in those embodiments where said species of DNA is circulating cell-free DNA and said sample is a blood fraction such as plasma or serum. For example, the medical condition may be a cell proliferative disorder, such as a tumor or cancer. In particular embodiments, the medical condition is a tumor or a cancer of an organ selected from the list consisting of: liver, lung, breast, colon, esophagus, prostate, ovary, cervix, uterus, testis, brain, bone marrow and blood; and/or said species of DNA may originate from cells of a tumor; particularly where such tumor is a carcinoma or cancer of an organ selected from the group consisting of: liver, lung, breast, colon, esophagus, prostate, ovary, cervix, uterus, testis, brain, bone marrow and blood.

In yet another particular embodiment of the present invention, said species of DNA originates from a cell type associated with a medical condition selected from the group consisting of: an infection/infectious disease, a wasting disorder, a degenerative disorder; an (auto)immune disorder, kidney disease, liver disease, inflammatory disease, acute toxicity, chronic toxicity, myocardial infarction, and a combination of any of the forgoing (such as sepsis) and/or with a cell proliferative disorder, particularly in those embodiments where said species of DNA is circulating cell-free DNA and said sample is a blood fraction such as plasma or serum. For example, the medical condition may be an infection/infectious disease, such as one caused by a bacterial, viral or protozoan pathogen, including a pathogen selected from the group consisting of: a retrovirus (such as HIV), a herpes virus (such as HSV, EBV, CMV, HHV or VSV), dengue virus, mycobacteria (e.g. *Mycobacterium tuberculosis*), and hantavirus. In certain embodiments, the medical condition is sepsis and/or excludes kidney disease.

In some aspects of the present invention, there exist embodiments wherein the biological sample is a tissue sample or a sample of biological fluid. In particular, the sample is whole blood or a blood fraction (e.g., such as plasma or serum). In alternative embodiments, the sample is biological fluid selected from the group consisting of: urine, saliva, sweat, ejaculate, teats, phlegm, vaginal secretion, vaginal wash and colonic wash. In more particular embodiments, the sample is a plasma or serum sample from the individual, or is urine from the individual in other embodiments, the sample is largely (or essentially) free from cells, and/or is not a whole blood and/or ejaculate sample.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1. Materials and Methods

Control Genomic DNA

We obtained intact human genomic DNA samples from a commercial vendor (Sigma Aldrich). Control DNA from one individual was diluted to yield 4 aliquots of 50 µL each a DNA concentration of 0.5 ng/µL. DNA concentration was measured using QUBIT® dsDNA BR Fluorometric Assay (Life Technologies). We sheared each aliquot using sonication with E220™ Focused-ultrasonicator (Covaris) as per manufacturer's instructions to achieve target fragment sizes were 150 bp, 300 bp, 500 bp and 1000 bp. The size distribution of DNA fragments was evaluated using the BioAnalyzer High Sensitivity Assay (Agilent Technologies, Inc.).

Control Plasma DNA

We obtained control plasma samples from healthy donors from a commercial vendor (BioreclamationIVT). Cell-free plasma DNA was extracted from 1 mL aliquots of plasma from 5 independently purchased samples using the QIAAMP® Circulating Nucleic Acid Kit (Qiagen). We modified the recommended protocol to elute in 100 µL volume and eluent was passed through the column twice. Plasma DNA was extracted with carrier RNA except when specifically indicated otherwise. Total DNA concentrations were measured using the QUBIT® dsDNA BR Fluorometric Assay (Life Technologies). The size distribution of DNA fragments was evaluated using the BioAnalyzer High Sensitivity Assay (Agilent).

Assay Design

We designed a multiplexed assay targeting 9 single copy genomic loci expected to be stable and least likely to be affected by copy number events in cancer patients. Five short PCR amplicons were designed with mean product size of ~71 bp (range 67-75 bp) and all corresponding probes were labeled with fluorescein amidite (FAM). Four long PCR amplicons were designed mean PCR product size of ~471 bp (range 439-522 bp) and all corresponding probes were labeled with 5-tetrachloro-fluorescein (TET). Primers and probes were designed using the PRIMERQUEST® tool (IDT). Primers/probes were manually evaluated to ensure they do not overlap with known polymorphic sites. In silico PCR was used to confirm each primer yielded a single product and no cross products when used in multiplex. Primer and probe sequences are reported in FIG. 1.

Droplet Digital PCR

A schematic presenting the steps involved in one application of digital droplet PCR to detect mutant and wild type genes in genomic DNA are shown in FIG. 2. Similarly, a multiplex ddPCR assay may be used to detect high molecular weight (HMW) DNA and low molecular weight (LMW) cfDNA in a biological sample containing both cfDNA and DNA derived from cells (e.g., DNA from peripheral blood cells).

All digital droplet PCR reactions were prepared at 25 µL volume using 12.50 µL of 2× Kapa Probe Fast Master Mix (Kapa Biosystems, USA), 1 µL of 5 mM dNTP Mix (Kapa), 1 µL of Droplet Stabilizer (RainDance Technologies, Lexington, Mass.), 1.25 µL of 20 uM of each primer (IDT) and 0.38 µL of 20 µM of each probe (IDT DNA, USA) and 2 µL of input DNA, and molecular biology grade water. Droplets were generated as per manufacturer's instructions using RAINDROP™ Digital PCR Source system (RainDance). Temperature cycling was performed using DNA ENGINE TETRAD® 2 (Bio-Rad Laboratories, Hercules, Calif.) with the following parameters: 1 cycle of 3 min at 95° C., 50 cycles of 15 sec at 95° C. and 1 min at 60° C. with a 0.5° C./sec ramp from 95° C. to 60° C., 1 cycle of 98° C. for 10 min and hold at 4° C. forever. Droplets fluorescence was measured using RAINDROP™ Digital PCR Sense system (RainDance).

Quantification of Plasma DNA

Analysis of fluorescence was performed using manufacturer's software that accompanies RAINDROP™. Identification of positive droplets requires setting fluorescence thresholds (gates) for each ddPCR assay. We compared results across intact genomic DNA and no template controls to assess thresholds for this assay. These thresholds were used for all future samples.

Figure 3:
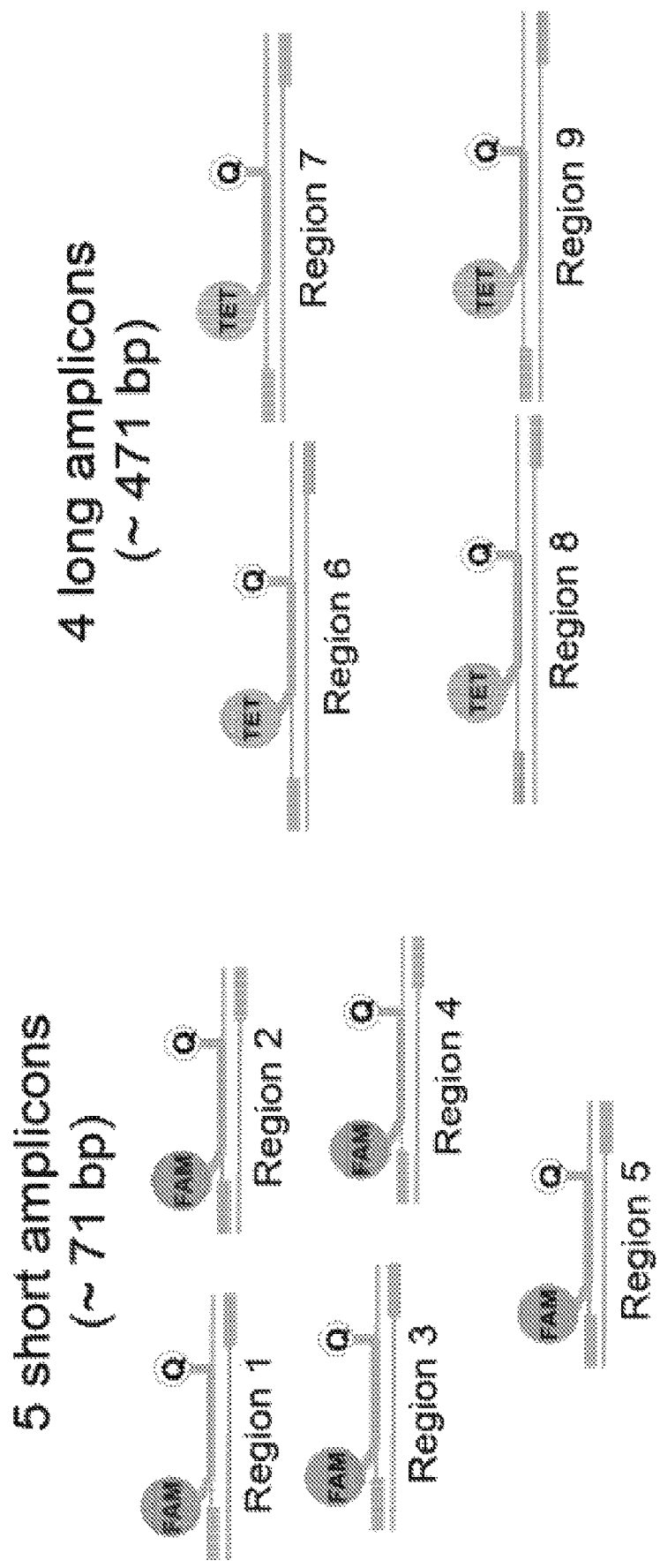
FIG. 3 presents an embodiment of the ddPCR assay design which produces five short amplicons (~71 bp in length) and four long amplicons (~471 bp in length). The nine genomic regions represent housekeeping regions. The fluorescent probes shown in the figure comprise quenchers indicated with a "Q" and the fluorophores fluorescein amidite (FAM) and 5-tetrachloro-fluorescein (TET), but any fluorophore known in the art can be conjugated to the probes used in the assay.
Figure 5:
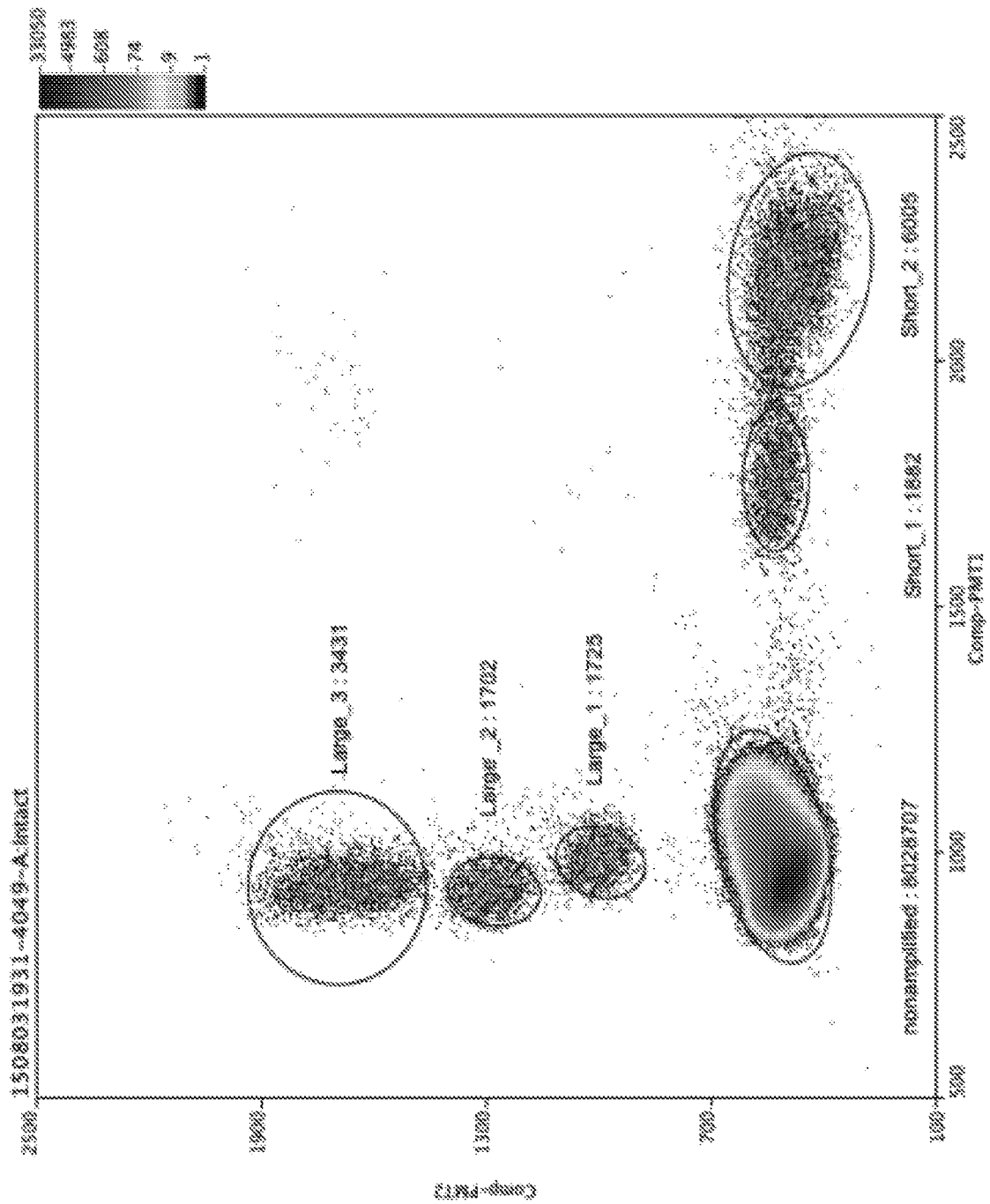
FIG. 5 shows fluorescence measurements for large amplicons and short amplicons with the ddPCR assay disclosed herein.

Based on the assay design, which is depicted in FIG. 3, we expect two populations of droplets on ddPCR, each representing the sum of products from the two amplicon sets. Therefore, the number of FAM-positive droplets (with the short PCR amplicon) represents 5 times the number of amplifiable haploid copies of the genome (ACs) with fragment sizes >71 bp (the average PCR amplicon size in the short set). This was used to calculate total amplifiable plasma DNA concentration. Similarly, the number of TET-positive droplets (with the long PCR products) represents 4 times the ACs with fragment sizes >471 bp (the average PCR amplicon size in the long set). This was used to calculate concentration of HMW plasma DNA. The difference between the two sets was taken to be the concentration of low molecular weight cfDNA. An example of this calculation is shown in FIG. 4. Quantification of fluorescence from short and large amplicons generated by the disclosed assay is depicted in FIG. 5.

Simulation of DNA Fragmentation and Expected Assay Performance

Simulations of DNA fragmentation were performed using R (code available upon request). We assumed a DNA molecule spanning 2500 bp on either side of the average amplicon size for each set. The length of this molecule was 5071 bp for the short amplicon set and 5471 bp for the long amplicon set. This molecule was mathematically fragmented by sampling from an exponential distribution with a rate representing the targeted fragment size (150, 300, 500 or 1000 bp). We determined that a molecule will be "missed" by an amplicon if a DNA break fell within the amplicon region (bound by 5' ends of either primers). We sampled 50,000 molecules to determine overall frequency of missed molecules for each combination of amplicon size and fragment size. The exponential distribution has been used to model DNA shearing by sonication previously.

Exome Sequencing

Whole genome sequencing libraries from plasma and genomic DNA were prepared using the THRUPLEX® DNA-Seq kit (Rubicon Genomics), as per manufacturer's instructions. Input cfDNA or sheared DNA was quantified using the ddPCR assay described herein and diluted to 10 μL volume. Sample specific barcodes were assigned to each library. Each library was quantified using the qPCR library quantification kits (Kapa). We pooled up to 8 libraries across 4 pools at equimolar concentrations in preparation for exome enrichment. Exome enrichment was performed using NimbleGen SeqCap EZ Human Exome v3 kit, as per manufacturer's instructions. We modified the protocol to use XGEN® Universal Blocking Oligos—TS HT-i5 and TS HT-i7 (Integrated DNA Technologies).

All enriched exome libraries were quantified using qPCR and pooled at equimolar concentrations for sequencing. Sequencing was performed on the MiSeq® using the TruSeq® v3 150-cycle kit (Illumina) to generate 75 bp paired-end reads and 6 bp barcode read.

Sequencing Data Analysis

Raw data from the sequencer was demultiplexed and converted to fastq files using Picard tools. Demulitplexing on sample-specific barcodes was performed allowing zero mismatches and requiring minimum base quality phred score of 30. Sequencing reads were aligned to the human genome hg19 using bwa v1.1. Aligned files were sorted and indexed using samtools v1.0. We estimated identified duplicate sequencing reads, estimated library complexity and estimated quality metrics (such as on-target reads) using Picard.

Example 2. Assessment of Assay Background

We evaluated the ddPCR assay using 3 template-free controls, 2 maize DNA samples and 2 canine DNA samples to assess background noise. The maximum number of positive droplets observed in template-free controls (limit of blank) was 28 and 20 for short and long amplicons respectively, equivalent to 6 and 5 ACs. The number of positive droplets across maize and canine DNA was higher than template-free controls likely due to cross-amplification across species for conserved genomic regions.

Figure 6:
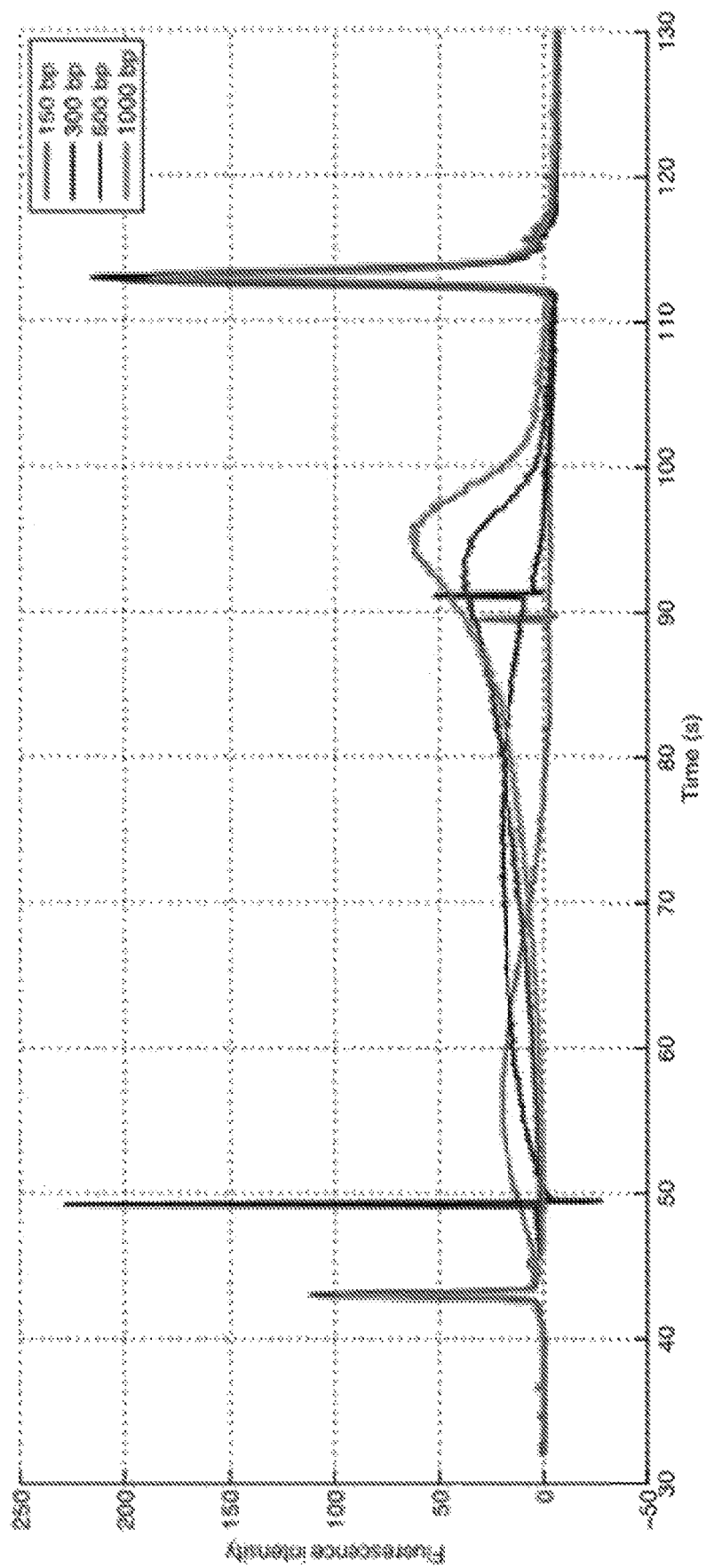
FIG. 6 depicts raw fluorescence intensity measurements from amplicons generated with fragmented DNA.
Figure 7:
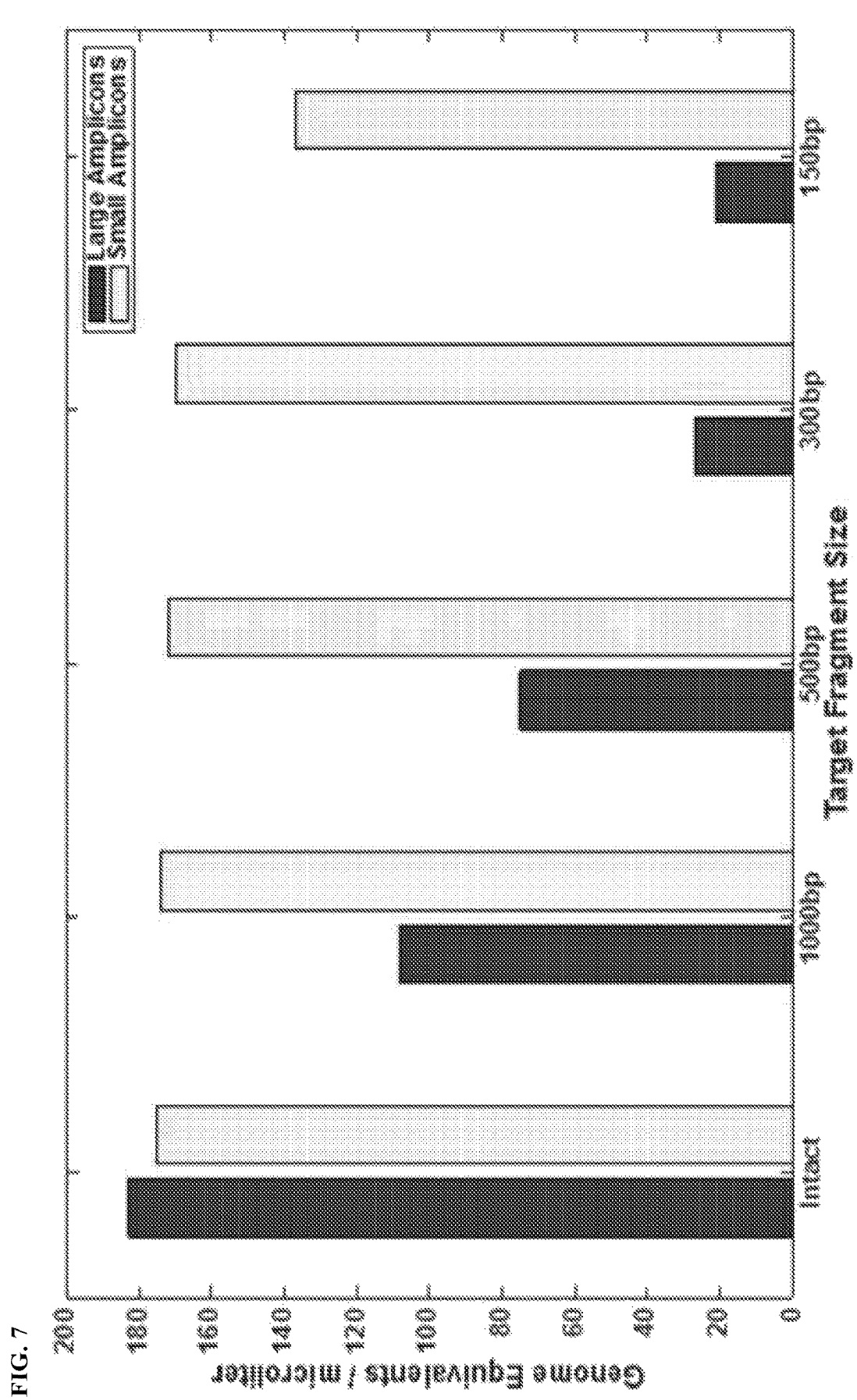
FIG. 7 depicts genome equivalents per microliter of sample for intact genomic DNA and fragmented genomic DNA having target fragment sizes of 1000 bp, 500 bp, 300 bp, and 150 bp as calculated from the fluorescence intensity measurements.

Example 3. Evaluation of the Integrity and Quantification of Sheared Genomic DNA The results of the ddPCR assessment of intact genomic DNA and fragmented genomic DNA are shown in FIG. 6 and FIG. 7. FIG. 6 presents a data set with the raw fluorescence intensity measurements from amplicons generated with fragmented DNA. FIG. 7 shows the genome equivalents per microliter of sample for intact genomic DNA and fragmented genomic DNA having target fragment sizes of 1000 bp, 500 bp, 300 bp, and 150 bp as calculated from the fluorescence intensity measurements.

The ddPCR assessment of intact genomic DNA at a QUBIT®-quantified concentration of 0.5 ng/μL yielded 175 short and 183 long amplifiable copies. The number of short ACs remained generally unaffected across sheared DNA samples except a significant drop with 150 bp fragments. In contrast, the number of long ACs dropped with each decrease in average fragment size (see FIG. 7).

Figure 8:
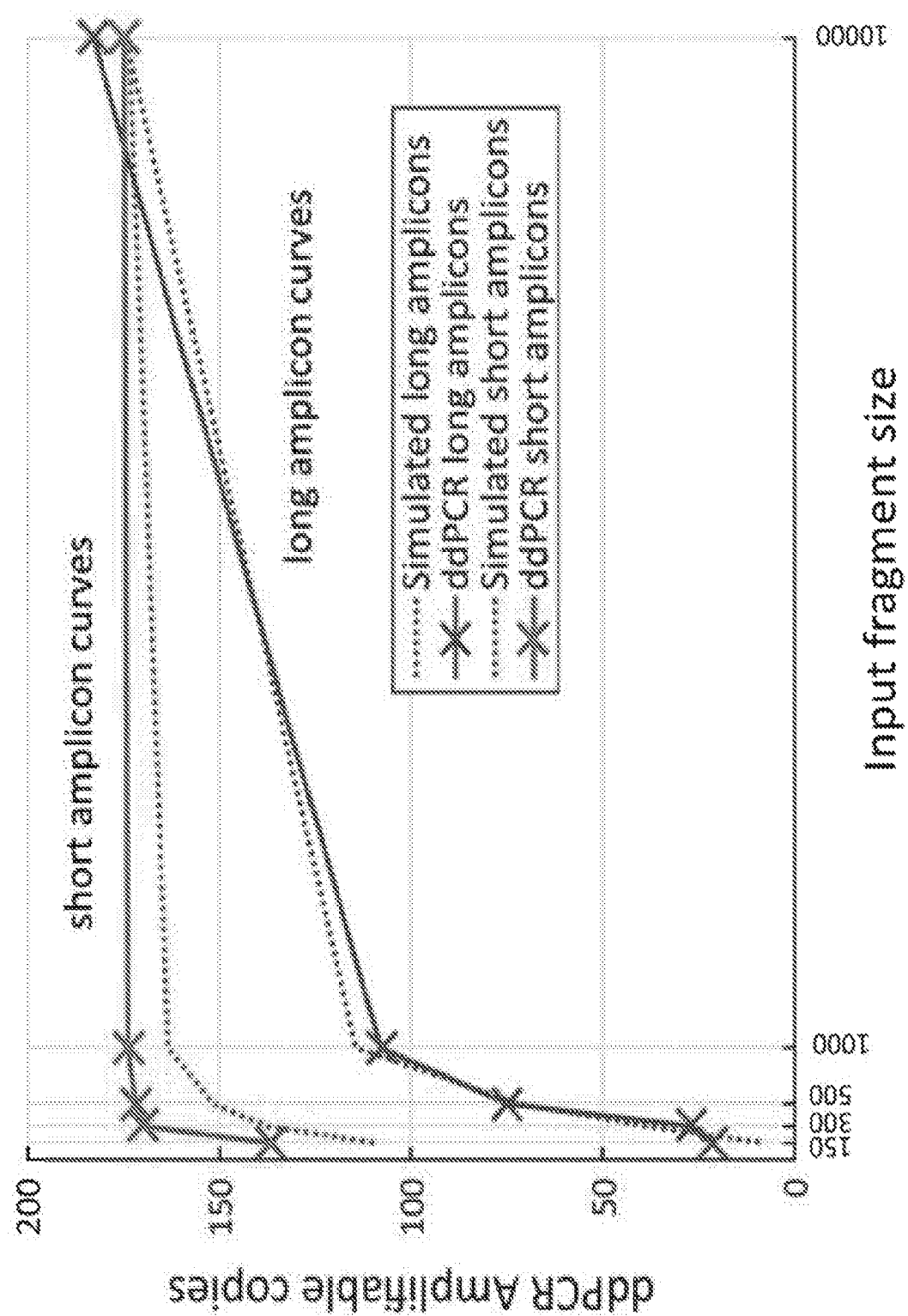
FIG. 8 shows actual curves (solid lines) generated with experimental data and simulated curves (dashed lines) based on exponential distributions with rates corresponding to average fragment sizes. ddPCR amplifiable copies at input fragment sizes of 150 bp, 300 bp, 500 bp, 1,000 bp, and 10,000 bp are indicated in each curve.

The trend in long ACs was similar to that observed in simulated data based on exponential distributions with rates corresponding to average fragment sizes. Surprisingly, simulated data underestimated the number of short ACs for all fragment sizes demonstrating that the ddPCR assay targeting short amplicons was more effective than estimated at producing ACs. The actual and simulated curves are presented in FIG. 8.

Example 4. Assessment of Library Yield for Sheared vs. Intact DNA

Whole genome sequencing libraries were generated using intact DNA or sheared DNA comprising 25%, 50%, or 75% DNA fragments of about 300 bp. The input amounts of DNA used to generate the libraries were either 2.5 ng or 5 ng. The library yield resulting from the various inputs was determined by qPCR.

Figure 9:
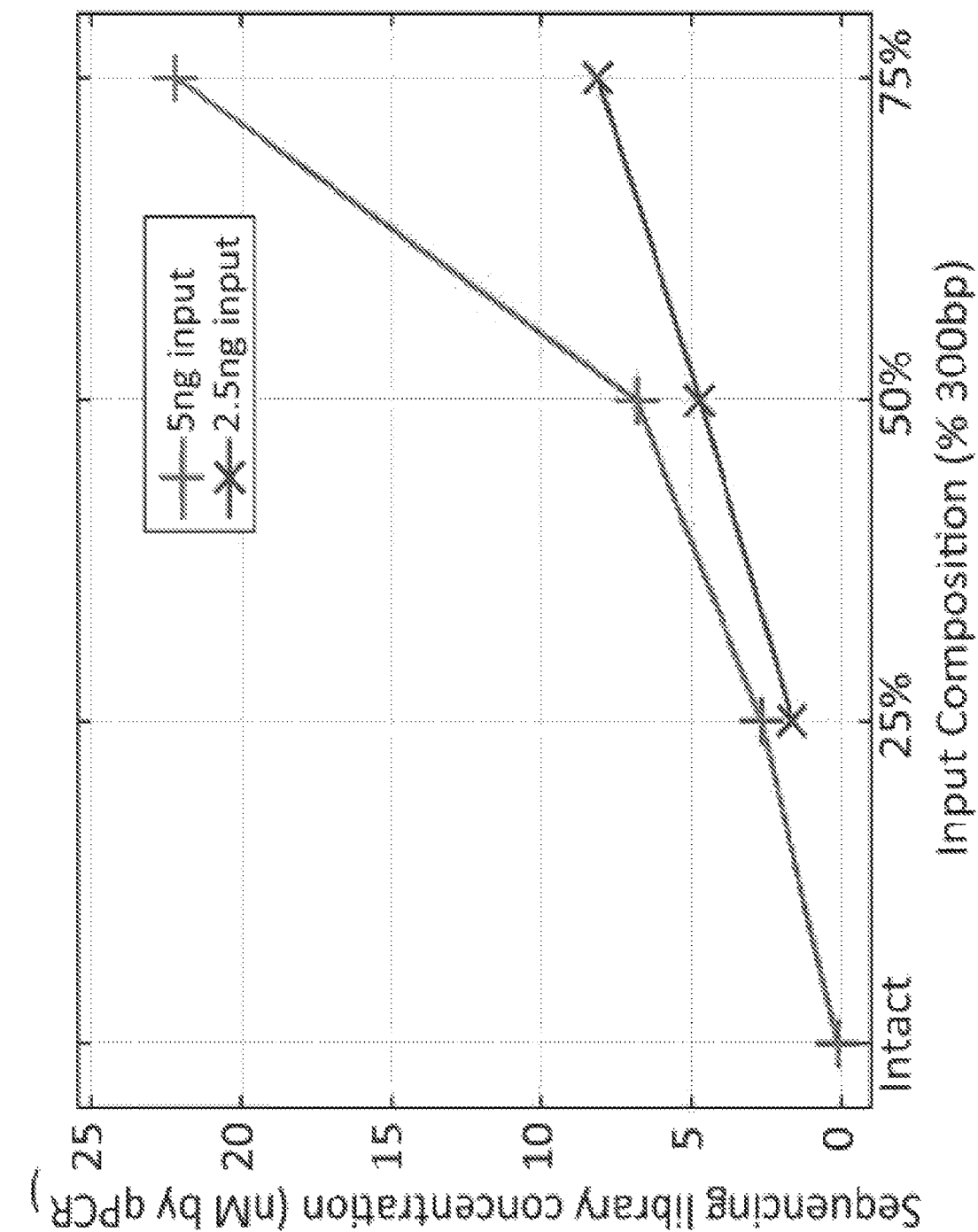
FIG. 9 depicts the sequencing library yield for sheared vs. intact DNA with intact DNA or sheared DNA comprising 25%, 50%, or 75% DNA fragments of about 300 bp.

As shown in FIG. 9, intact DNA produced no detectable amount of library sequences. In contrast, sheared DNA produced increasing yields of library sequences as the relative percentage of DNA fragments of about 300 bp increased. The greatest library yield resulted from 5 ng of DNA containing 75% fragments of about 300 bp.

These results indicate that intact DNA present in biological samples with cfDNA generally does not contribute to the sequencing library yield. Moreover, as the amount of low molecular weight cfDNA increases in a biological sample the resulting yield of the library produced from this cfDNA will likewise increase.

Example 5. Preparation of cfDNA from Biological Samples with Differing Amounts of HMW and LMW DNA Preparation of cfDNA for whole genome sequencing assumes pre-fragmented DNA, and no further shearing of the DNA is performed. However, results vary from one preparation of cfDNA to another. To investigate the causes for this variation cfDNA was prepared from two biological samples and the HMW DNA (i.e., large amplicons) and LMW cfDNA (i.e., small amplicons) were quantified using the ddPCR method described in Example 1.

Figure 10A:
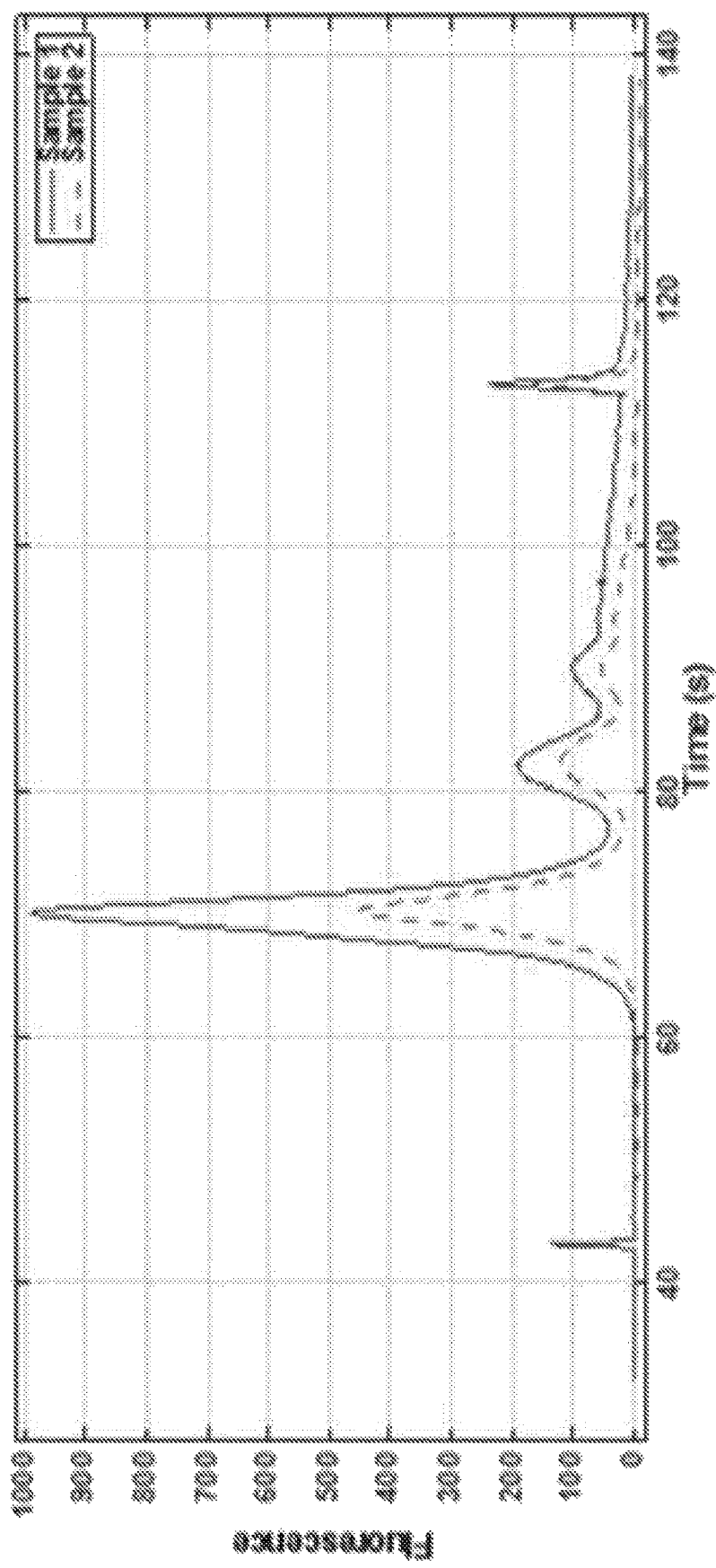
FIG. 10A shows the fluorescence generated from two biological samples with differing amounts of HMW and LMW DNA using the multiplexed ddPCR assay.
Figure 10B:
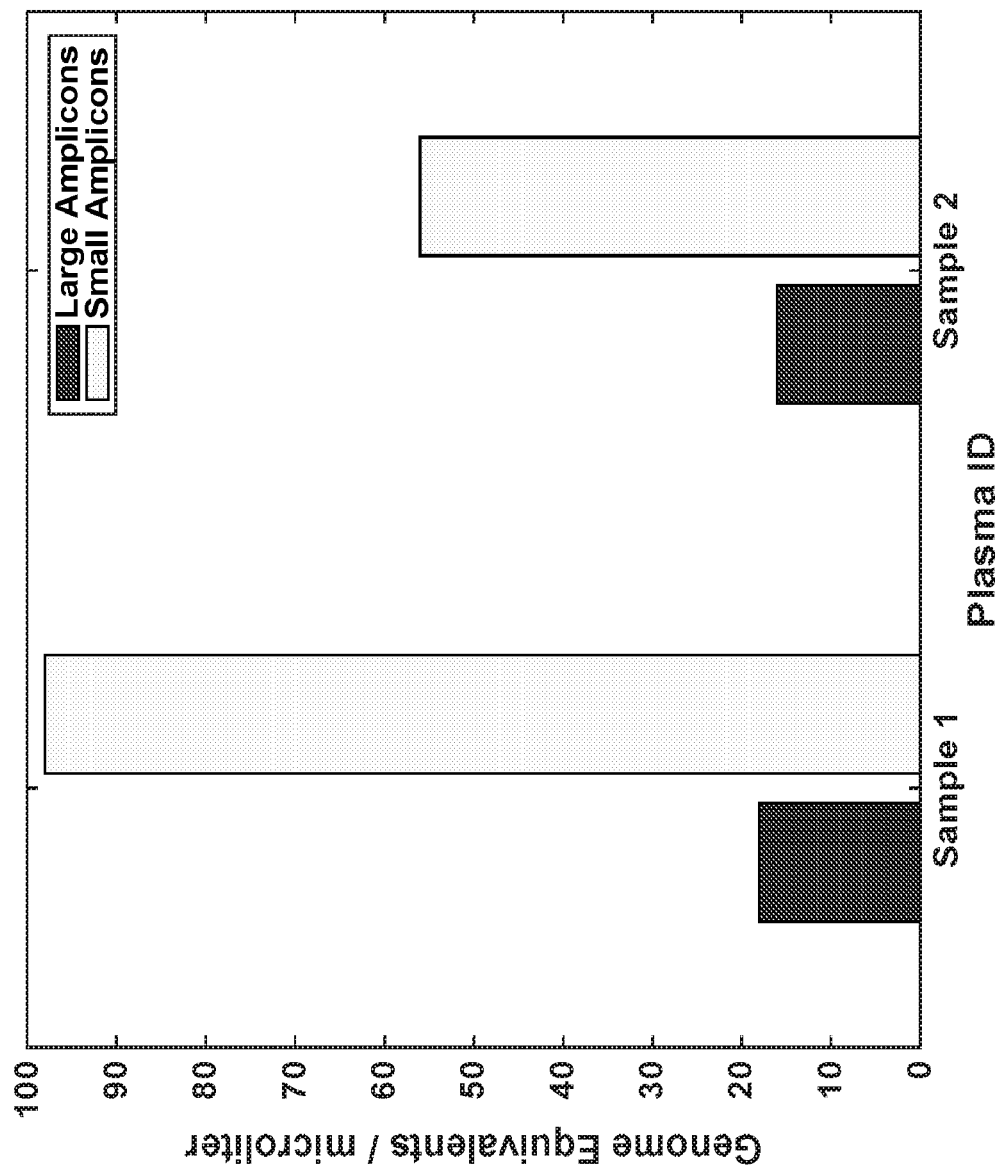
FIG. 10B depicts a bar graph indicating the relative amounts of large amplicons and small amplicons produced from each sample with the multiplexed ddPCR assay.

Sample 1 generated a greater number of ACs than did Sample 2 using similar amounts of starting material (compare the greater fluorescence observed with ddPCR of DNA from Sample 1 to that observed with ddPCR of DNA from Sample 2 in FIG. 10A). When the relative amounts of large amplicons and small amplicons produced from each sample were compared it was seen that Sample 1 had a larger ratio of small amplicons to large amplicons than Sample 2 (see FIG. 10B). These results suggest that the assessment of HMW and LMW DNA in biological samples using the methods disclosed herein provides an accurate indicator of the quality and quantity of cfDNA present in the samples.

Figure 11:
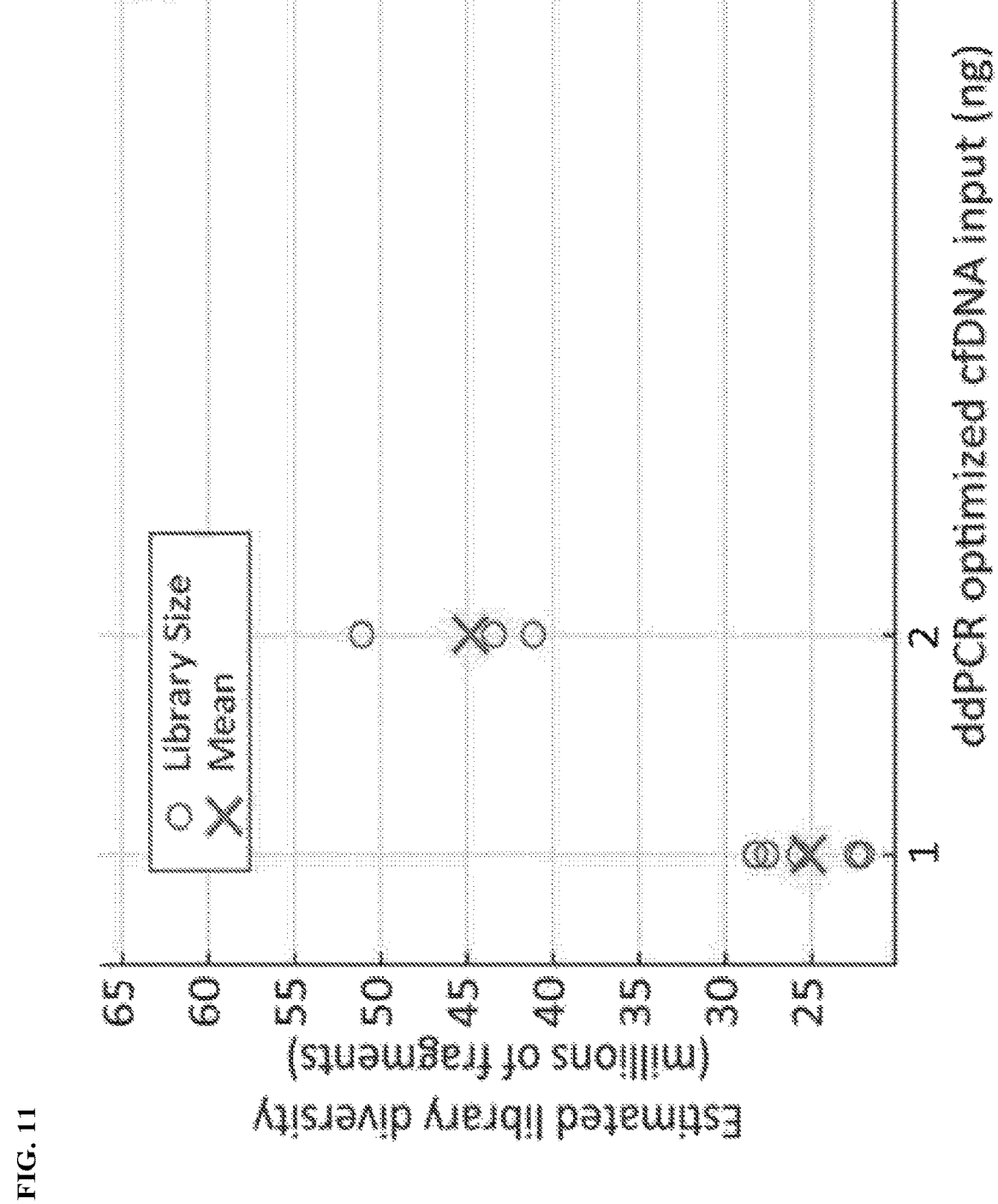
FIG. 11 depicts sequencing library diversity and size in relationship to ddPCR optimized cfDNA input.

Example 6. Diversity of ddPCR-Optimized Plasma Exome Libraries ddPCR assessment of cfDNA in control plasma samples was used to guide library preparation. Sequencing libraries were assessed for diversity (i.e., "estimated library diversity") and duplication rate (i.e., "number of genome equivalents"). Library diversity and size were related to input DNA as quantified using the ddPCR assay (see FIG. 11). As the amount of ddPCR optimized cfDNA used for library preparation increased so did the library diversity and duplication rate.

Example 7. Assessment of the Effects of Upstream Processing of Biological Samples on cfDNA Amplifiable Copies Prior to analysis of cfDNA with whole genome sequencing several upstream processes are required to collect and process biological samples. These upstream processes include such things as collection of biological samples (e.g., blood, urine, saliva) and extraction of DNA from the biological samples. The upstream processes can affect the downstream analysis and sequencing of cfDNA.

Figure 12:
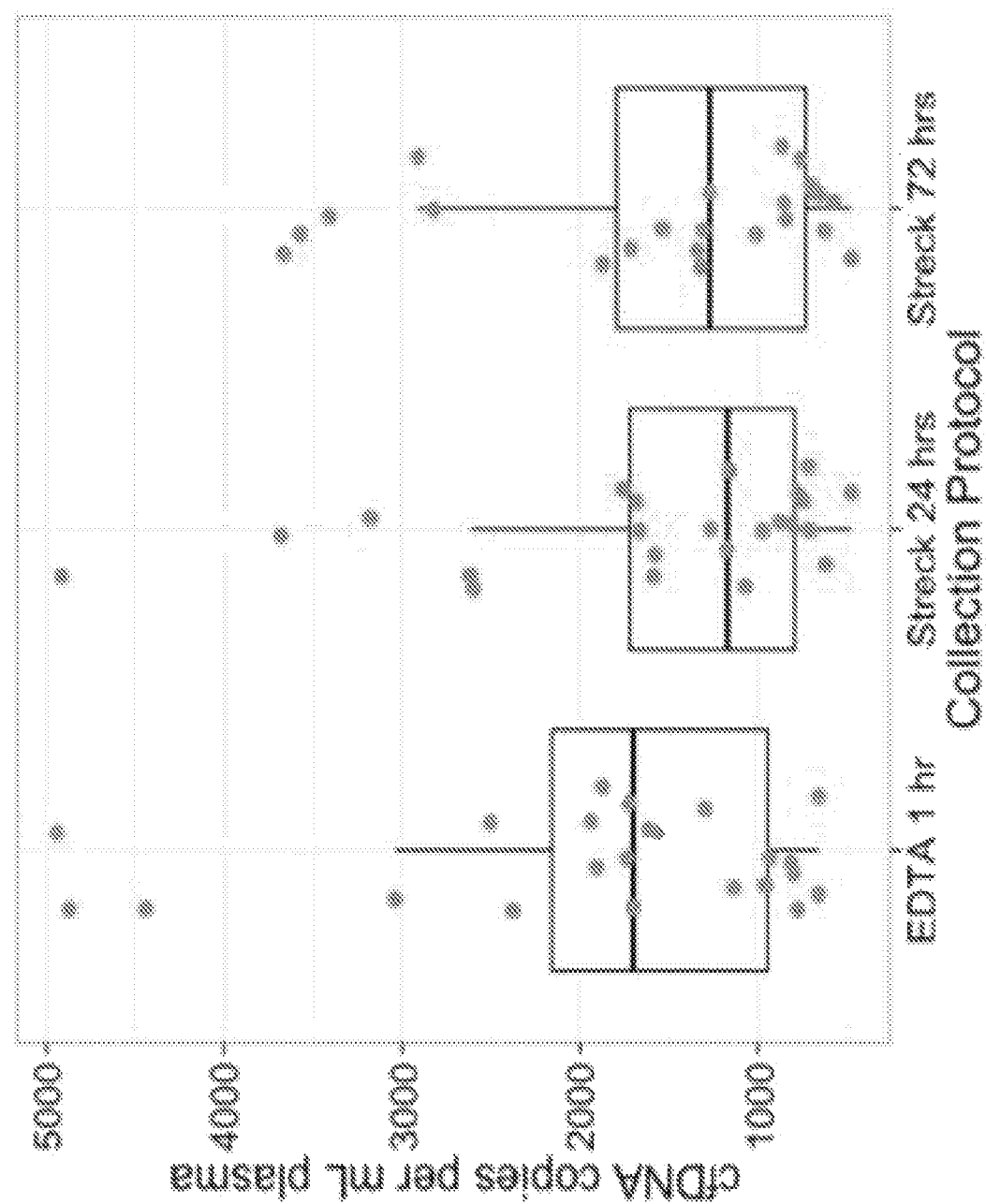
FIG. 12 presents the effect of several blood collection protocols on the number of cfDNA amplifiable copies per mL of plasma.

The ddPCR assay described in Example 1 was used to evaluate the effect of various blood collection protocols. The protocols employed blood collection tubes containing EDTA as the anticoagulant or Streck cfDNA blood collection tubes (Streck Laboratories, Omaha, Nebr.) containing a proprietary preservative (Streck Laboratories). The effect of the various blood collection protocols on the number of cfDNA amplifiable copies per mL of plasma is shown in FIG. 12.

Figure 13A:
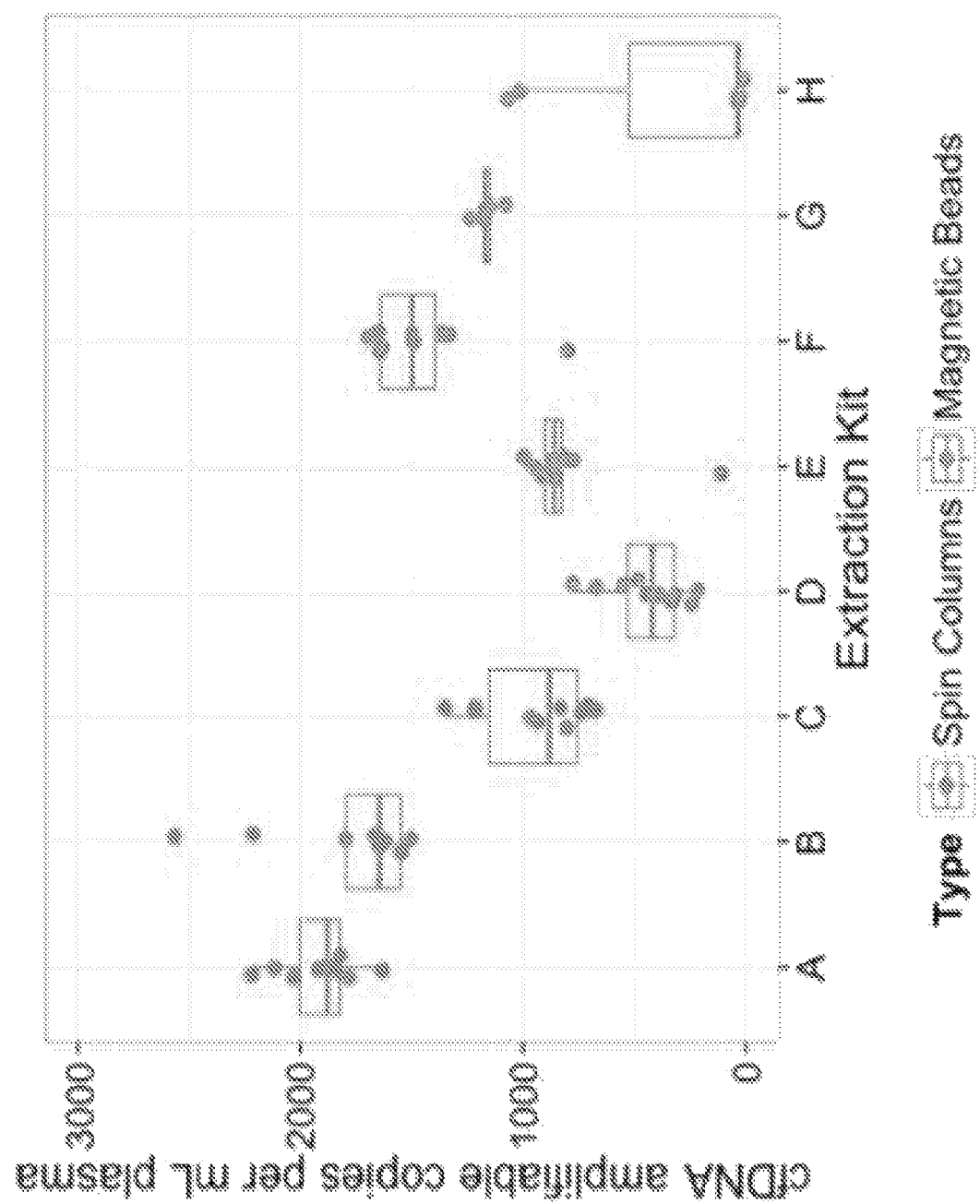
FIGS. 13A and 13B show that impact of several DNA extraction kits on the amount of cfDNA amplifiable copies obtained from plasma samples. Extraction kits identified as A, B, and C utilize spin columns while extraction kits identified as D, E, F, G, and H utilize magnetic beads.
Figure 13B:
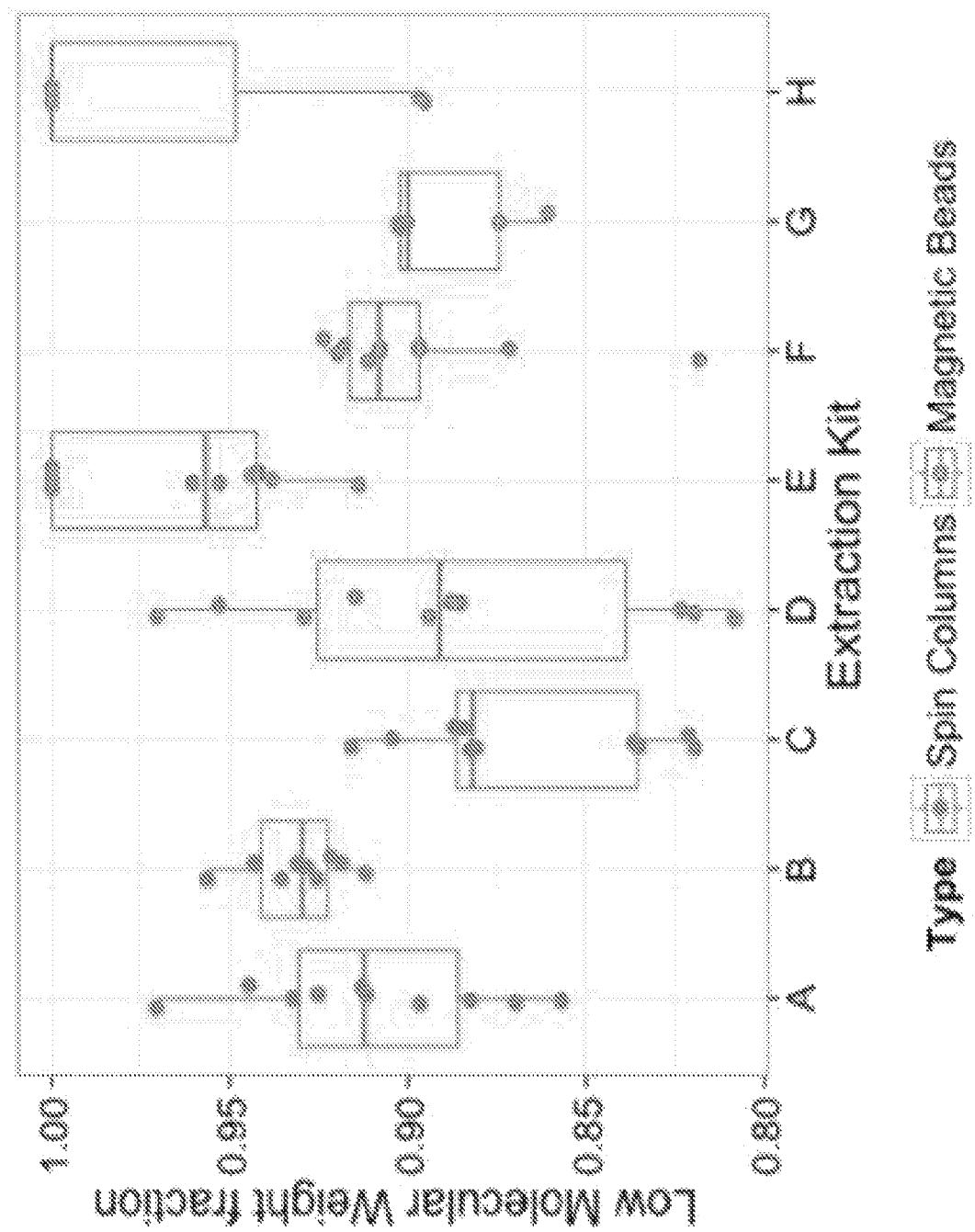

DNA may be extracted from biological samples in several ways, and this upstream process also affects the downstream analysis and sequencing of cfDNA. Several DNA extraction kits using spin columns or magnetic beads were evaluated for their effect on the cfDNA in plasma samples. The DNA in each sample was extracted per the manufacturer's instructions in each kit. cfDNA amplifiable copies per mL plasma in each biological sample were determined with the ddPCR assay described in Example 1. The results of the analysis presented in FIGS. 13A and 13B show that the extraction kit used can significantly impact the amount of cfDNA amplifiable copies obtained from plasma samples.

Figure 14:
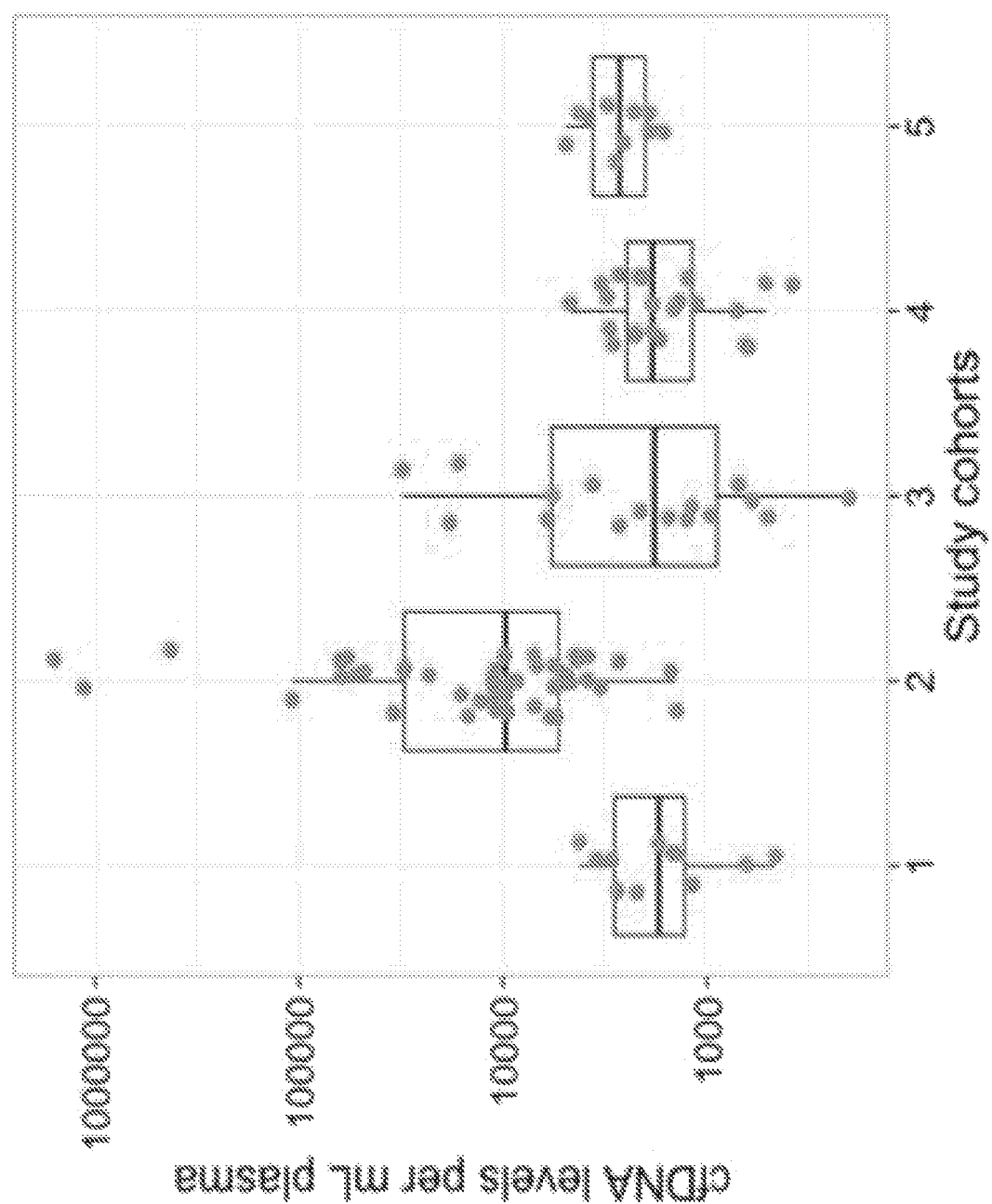
FIG. 14 depicts an analysis of the quality of biological samples from different study cohorts using the multiplexed ddPCR assay.

The ddPCR assay described herein can also be used to analyze the quality of biological samples from different study cohorts. Such an analysis was performed resulting in the data shown in FIG. 14. This quality assessment across study cohorts can be useful in interpreting the results of the data and explaining differences observed across the cohorts. For example, if one cohort has a relatively high level of cfDNA amplifiable copies in its biological samples the subsequent whole genome sequencing and analysis may identify genetic indicators of disease that are not detectable in other cohorts due the poor quality or relatively low levels of cfDNA amplifiable copies in their biological samples.

The experimental data outlined above demonstrate that the multiplexed ddPCR assay allows accurate and precise assessment of amplifiable copies and integrity of cfDNA from small amounts of input (e.g., picograms of DNA). Upfront quality assessment with the multiplexed ddPCR assay can optimize downstream analysis and sequencing. Moreover, the multiplexed ddPCR assay provides reliable metrics for optimization of pre-analytical factors such as plasma processing and extraction.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Bianchi D W, Parker R L, Wentworth J, Madankumar R, Saffer C, Das A F, et al. DNA sequencing versus standard prenatal aneuploidy screening. The New England journal of medicine 2014; 370:799-808.
2. Leary R J, Sausen M, Kinde I, Papadopoulos N, Carpten J D, Craig D, et al. Detection of chromosomal alterations in the circulation of cancer patients with whole-genome sequencing. Science translational medicine 2012; 4:162ra54.
3. Chan K C, Jiang P, Zheng Y W, Liao G J, Sun H, Wong J, et al. Cancer genome scanning in plasma: Detection of tumor-associated copy number aberrations, single-nucleotide variants, and tumoral heterogeneity by massively parallel sequencing. Clinical chemistry 2013; 59:211-24.
4. Murtaza M, Dawson S J, Tsui D W, Gale D, Forshew T, Piskorz A M, et al. Non-invasive analysis of acquired resistance to cancer therapy by sequencing of plasma DNA. Nature 2013; 497:108-12.
5. Chiu R W, Akolekar R, Zheng Y W, Leung T Y, Sun H, Chan K C, et al. Non-invasive prenatal assessment of trisomy 21 by multiplexed maternal plasma DNA sequencing: Large scale validity study. Bmj 2011; 342: c7401.
6. Lo Y M, Chan K C, Sun H, Chen E Z, Jiang P, Lun F M, et al. Maternal plasma DNA sequencing reveals the genome-wide genetic and mutational profile of the fetus. Sci Transl Med 2010; 2:61ra91.
7. De Vlaminck I, Valantine H A, Snyder™, Strehl C, Cohen G, Luikart H, et al. Circulating cell-free DNA enables noninvasive diagnosis of heart transplant rejection. Sci Transl Med 2014; 6:241ra77.
8. Forshew T, Murtaza M, Parkinson C, Gale D, Tsui D W, Kaper F, et al. Noninvasive identification and monitoring of cancer mutations by targeted deep sequencing of plasma DNA. Science translational medicine 2012; 4:136ra68.
9. Dawson S J, Tsui D W, Murtaza M, Biggs H, Rueda O M, Chin S F, et al. Analysis of circulating tumor DNA to monitor metastatic breast cancer. The New England journal of medicine 2013; 368:1199-209.
10. Bettegowda C, Sausen M, Leary R J, Kinde I, Wang Y, Agrawal N, et al. Detection of circulating tumor DNA in early- and late-stage human malignancies. Science translational medicine 2014; 6:224ra24.
11. Devonshire A S, Whale A S, Gutteridge A, et al. Towards standardisation of cell-free DNA measurement in plasma: controls for extraction efficiency, fragment size bias and quantification. Analytical and Bioanalytical Chemistry. 2014; 406(26):6499-6512.

What is claimed is:

1. A method of determining and optimizing the integrity of cell free DNA (cfDNA) in a biological sample for library preparation, the method comprising the steps of:
   a) obtaining a biological sample comprising cfDNA;
   b) contacting the biological sample with at least a first primer/probe set and at least a second primer probe/set, each of which comprises at least one oligonucleotide probe that is detectably labeled and at least two oligonucleotide primers and the labels are different for each primer/probe set, under conditions such that the first primer/probe set anneals to a first target sequence of less than 300 bp in length and the second primer/probe set anneals to a second target sequence of 300 bp or greater in length;
   c) amplifying, if present, the first target sequence and the second target sequence; and
   d) monitoring for detection of the label of the oligonucleotide probe from the first primer/probe set as an indication of hybridization to the first target sequence and detection of the label of the oligonucleotide probe from the second primer/probe set as an indication of hybridization to the second target sequence;
   e) determining the integrity of the cfDNA by calculating the ratio of the level of detection of the label of the oligonucleotide probe from the first primer/probe set to the level of detection of the label of the oligonucleotide probe from the second primer/probe set,
   wherein a greater ratio indicates increased integrity of cfDNA in the biological sample; and
   f) generating a sequencing library with the cfDNA based on the optimized integrity of the cfDNA,
   wherein an increase in the amount of optimized cfDNA used for library preparation increases the library diversity and duplication rate.

2. The method of claim 1, wherein the oligonucleotide primers have a nucleotide sequence length of about 10 to about 150.

3. The method of claim 1, wherein the oligonucleotide probes have a nucleotide sequence length of about 10 to about 50.

4. The method of claim 1, wherein the first target sequence and the second target sequence are from at least one housekeeping gene.

5. The method of claim 4, wherein the at least one housekeeping gene is selected from the group consisting of ACTB (Beta-actin), GAPDH (Glyceraldehyde 3-phosphate dehydrogenase), RPLP0 (60 S acidic ribosomal protein P0), GUSB (beta-glucuronidase), and TFRC (transferring receptor 1).

6. The method of claim 1, wherein the first primer/probe set comprises at least one oligonucleotide probe and at least two oligonucleotide primers each comprising an oligonucleotide sequence selected from the group consisting of SEQ ID NOs: 13-27.

7. The method of claim 1, wherein the second primer/probe set comprises at least one oligonucleotide probe and at least two oligonucleotide primers each comprising an oligonucleotide sequence selected from the group consisting of SEQ ID NOs: 1-12.

8. The method of claim 1, wherein the first primer/probe set comprises at least two, at least three, at least four, or at least five oligonucleotide probes that are detectably labeled and at least four, at least six, at least eight, or at least 10 oligonucleotide primers, each of which anneals to a target sequence of less than 300 bp, and wherein detection of the labels of the oligonucleotide probes from the first primer probe/set are averaged to determine the detection of the labels.

9. The method of claim 1, wherein the second primer/probe set comprises at least two, at least three, at least four, or at least five oligonucleotide probes that are detectably labeled and at least four, at least six, at least eight, or at least 10 oligonucleotide primers, each of which anneals to a target sequence of 300 bp or greater in length, and wherein detection of the labels of the oligonucleotide probes from the second primer probe/set are averaged to determine the detection of the labels.

10. The method of claim 1, wherein the amplifying of the target sequences occurs with a digital PCR technique selected from droplet digital PCR (ddPCR), BEAMing (beads, emulsion, amplification, and magnetic), and microfluidic chips.

11. The method of claim 10, wherein the digital PCR technique is multiplexed ddPCR, and amplifiable copies (ACs) of cfDNA in the biological sample are estimated by:
   (i) dividing the number of positive droplets indicating hybridization to the first target sequence by the number of oligonucleotide probes in the first primer/probe set;
   (ii) dividing the number of positive droplets indicating hybridization to the second target sequence by the number of oligonucleotide probes in the second primer/probe set; and
   (iii) subtracting (ii) from (i) to estimate ACs of cfDNA in the biological sample.

12. The method of claim 1, wherein the oligonucleotide probes are detectably labeled with a fluorescent label selected from the group consisting of 5 or 6-carboxyfluorescein, Fluorescein, 5-tetrachloro-fluorescein, sulforhodamine sulfonyl chloride, 2',5,5',6-tetrachloro-7'-{12-[di(propan-2-yl)amino]-15-hydroxy-3-oxo-11,13-dioxa-4-aza-12-phosphapentadecyl}-4'-methyl-3-oxo-3H-spiro[2-benzofuran-1,9'-xanthene]-3',6'-diyl bis(2,2-dimethylpropanoate, and 6,8-difluoro-7-hydroxy-4-methylcoumarin.

13. The method of claim 12, wherein the fluorescent labels are 5- or 6-carboxyfluorescein and 5-tetrachlorofluorescein.

14. The method of claim 1, wherein the first primer/probe set detects at least one, at least two, at least three, at least four, or at least five target sequences of about 50 bp to about 100 bp in length.

15. The method of claim 1, wherein the second primer/probe set detects at least one, at least two, at least three, at least four, or at least five target sequences of about 300 bp to about 1000 bp in length.

16. The method of claim 1, wherein the sequencing library is an exome library.

17. The method of claim 1, wherein the biological sample is divided into aliquots and each aliquot undergoes a different upstream process to evaluate how upstream processing affects the integrity of cfDNA in the biological sample.

18. The method of claim 1, wherein the biological sample is a biofluid selected from the group consisting of blood, plasma, serum, saliva, urine, tears, and cerebral spinal fluid.

19. The method of claim 1, wherein detection of the labels of the oligonucleotide probes occurs with a flow cytometer or a droplet reader.

\* \* \* \* \*

SEQUENCE LISTING

<160> NUMBER OF SEQ ID NOS: 27

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
tctatgctcc ctctgtgtta ga                                    22

<210> SEQ ID NO 2
<211> LENGTH: 24
<212> TYPE: DNA
<213> ORGANISM: Artificial Sequence
<220> FEATURE:
<223> OTHER INFORMATION: Probe

<400> SEQUENCE: 2
agcaaggtgc cctgagaaga caat                                  24

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tccaggaatt cacccgaaac                                       20

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
cagacaagat gaggaggtac aaa                                   23

<210> SEQ ID NO 5
<211> LENGTH: 24
<212> TYPE: DNA
<213> ORGANISM: Artificial Sequence
<220> FEATURE:
<223> OTHER INFORMATION: Probe

<400> SEQUENCE: 5
attgagcctg tgcctggcta gaaa                                  24

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
agctgtgagt agaggagtct t                                     21

<210> SEQ ID NO 7
<211> LENGTH: 22
<212> TYPE: DNA
<213> ORGANISM: Artificial Sequence

```
<220> FEATURE:
<223> OTHER INFORMATION: Primer

<400> SEQUENCE: 7
aaagaggtct tgccaggtat tc                                              22

<210> SEQ ID NO 8
<211> LENGTH: 24
<212> TYPE: DNA
<213> ORGANISM: Artificial Sequence
<220> FEATURE:
<223> OTHER INFORMATION: Probe

<400> SEQUENCE: 8
atagggcttc aggccaaaca tggt                                            24

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
agctcactgc agccttaatc                                                 20

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gtctccagga tagctgctta tg                                              22

<210> SEQ ID NO 11
<211> LENGTH: 24
<212> TYPE: DNA
<213> ORGANISM: Artificial Sequence
<220> FEATURE:
<223> OTHER INFORMATION: Probe

<400> SEQUENCE: 11
tttgggactg gcctttgaag ctct                                            24

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
tgcatgtgag caccaagt                                                   18

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
cttgtacctg gtgttcggtt at                                              22
```

```
<210> SEQ ID NO 14
<211> LENGTH: 25
<212> TYPE: DNA
<213> ORGANISM: Artificial Sequence
<220> FEATURE:
<223> OTHER INFORMATION: Probe

<400> SEQUENCE: 14
agcctctctc ctctgcaacc tgata                                          25

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gtaggctggg tagccaaatc                                                20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ccagcccaag atggatgaat                                                20

<210> SEQ ID NO 17
<211> LENGTH: 23
<212> TYPE: DNA
<213> ORGANISM: Artificial Sequence
<220> FEATURE:
<223> OTHER INFORMATION: Probe

<400> SEQUENCE: 17
tgcagttgtt ccgaggtgac aca                                            23

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
ctcttctttc ctttcagcaa cac                                            23

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gcggtggaag tcattctgat a                                              21

<210> SEQ ID NO 20
<211> LENGTH: 26
<212> TYPE: DNA
<213> ORGANISM: Artificial Sequence
<220> FEATURE:
<223> OTHER INFORMATION: Probe
```

<400> SEQUENCE: 20
tggagttggc attggaagct tattct                                          26

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
tctctctctc tccagtgaac aa                                              22

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gagggccaca gattggtatt                                                 20

<210> SEQ ID NO 23
<211> LENGTH: 26
<212> TYPE: DNA
<213> ORGANISM: Artificial Sequence
<220> FEATURE:
<223> OTHER INFORMATION: Probe

<400> SEQUENCE: 23
aatgagatac gagggttgtt gctggg                                          26

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gatcacttag ctcaggaaac aaac                                            24

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
actgaaaggt cagattcagg ag                                              22

<210> SEQ ID NO 26
<211> LENGTH: 23
<212> TYPE: DNA
<213> ORGANISM: Artificial Sequence
<220> FEATURE:
<223> OTHER INFORMATION: Probe

<400> SEQUENCE: 26
atcgccttga tcaacagcct cca                                             23

<210> SEQ ID NO 27

```
<211> LENGTH: 20
<212> TYPE: DNA
<213> ORGANISM: Artificial Sequence
<220> FEATURE:
<223> OTHER INFORMATION: Primer

<400> SEQUENCE: 27
taccggtttg tgtccaagag                                                    20
```